US009718778B2

(12) United States Patent
Zhang et al.

(10) Patent No.: US 9,718,778 B2
(45) Date of Patent: Aug. 1, 2017

(54) MIXED DISULFIDE CONJUGATES OF THIENOPYRIDINE COMPOUNDS AND USES THEREOF

(71) Applicant: The Regents of the University of Michigan, Ann Arbor, MI (US)

(72) Inventors: Haoming Zhang, Ann Arbor, MI (US); Paul Hollenberg, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/758,736

(22) PCT Filed: Jan. 6, 2014

(86) PCT No.: PCT/US2014/010348
§ 371 (c)(1),
(2) Date: Jun. 30, 2015

(87) PCT Pub. No.: WO2014/109987
PCT Pub. Date: Jul. 17, 2014

(65) Prior Publication Data
US 2015/0353492 A1    Dec. 10, 2015

Related U.S. Application Data

(60) Provisional application No. 61/750,633, filed on Jan. 9, 2013.

(51) Int. Cl.
| | |
|---|---|
| *C07D 211/72* | (2006.01) |
| *C07D 405/12* | (2006.01) |
| *C07K 5/093* | (2006.01) |
| *A61K 31/445* | (2006.01) |
| *A61K 38/06* | (2006.01) |
| *A61K 47/48* | (2006.01) |
| *A61K 31/501* | (2006.01) |
| *C07D 401/12* | (2006.01) |
| *A61K 45/06* | (2006.01) |
| *A61K 31/4525* | (2006.01) |
| *A61K 31/4545* | (2006.01) |

(52) U.S. Cl.
CPC .......... *C07D 211/72* (2013.01); *A61K 31/445* (2013.01); *A61K 31/4525* (2013.01); *A61K 31/4545* (2013.01); *A61K 31/501* (2013.01); *A61K 38/06* (2013.01); *A61K 45/06* (2013.01); *A61K 47/48023* (2013.01); *A61K 47/48038* (2013.01); *A61K 47/48061* (2013.01); *A61K 47/48246* (2013.01); *C07D 401/12* (2013.01); *C07D 405/12* (2013.01); *C07K 5/0819* (2013.01)

(58) Field of Classification Search
CPC ... C07D 211/72; C07D 401/12; C07D 405/12
USPC .................................................. 546/194, 216
See application file for complete search history.

(56) References Cited

U.S. PATENT DOCUMENTS 6,610,708 B1 * 8/2003 Asai .................... C07D 205/04
514/327

FOREIGN PATENT DOCUMENTS

| EP | 1063230 | 12/2000 |
| JP | 2001-131067 | 5/2001 |
| KR | 10-2001-0041367 | 5/2001 |

OTHER PUBLICATIONS

Muller et al. "Lipophilic disulfide . . . " Int. j. Pharmaceutics v.57, p. 41-47 (1989).*
Patani et al. "Bioisosterism . . . " Chem. Rev. v.96, p. 3147-3176 (1996).*
Vrudhula et al. "Reductively activat . . . " Bioorg. Med. Chem. Lett, v. 12, p. 3591-94 (2002).*
Hagihara et al. "Biotransformation of Prasugrel, a Novel Thienopyridine Antiplatelet Agent, to the Pharmacologically Active Metabolite", Drug Metabolism and Disposition, 2010, vol. 38, No. 6, pp. 898-904.
Algaier et al. "Interaction of the active metabolite of prasugrel, R-138727, with cysteine 97 and cysteine 175 of the human P2Y12 receptor" J Thromb Haemost, 2008, 6(11):1908-1914.
Bouman et al. "Paraoxonase-1 is a major determinant of clopidogrel efficacy." Nat Med, 2011, 17(1):110-116.
Dansette et al. "Metabolic oxidative cleavage of thioesters: evidence for the formation of sulfenic acid intermediates in the bioactivation of the antithrombotic prodrugs ticlopidine and clopidogrel." Chem Res Toxicol, 2009, 22(2):369-373.
Dansette et al. "Cytochromes P450 catalyze both steps of the major pathway of clopidogrel bioactivation, whereas Daraoxonase catalyzes the formation of a minor thiol metabolite isomer" Chem Res Toxicol, 2012, 25(2):348-356.
Dansette et al. "Metabolic activation of prasugrel: nature of the two competitive pathways resulting in the opening of its thiophene ring." Chem Res Toxicol, 2012, 25(5):1058-1065.
Dansette et al. "Formation and fate of a sulfenic acid intermediate in the metabolic activation of the antithrombotic prodrug prasugrel." Chem Res Toxicol, 2010, 23(7):1268-1274.
Dick et al. "Clopidogrel Resistance: case reports of CYP2C19 gene variants in suspected coronary stent thrombosis." Heart Lung Circ, 2011, 20(10):657-658.
Ding et al. "Inactivation of the human P2Y12 receptor by thiol reagents requires interaction with both extracellular cysteine residues, Cys17 and Cys270." Blood, 2003, 101(10):3908-3914.
Farid et al. "The disposition of prasugrel, a novel thienopryidine, in humans". Drug Metabolism and Disposition, 2007, vol. 35, No. 7, pp. 1096-1104.
Fayed et al. "Separation and determination of clopidogrel and its impurities by capillary electrophoresis." J Pharm Biomed Anal, 2009, 49(2):193-200.
Freedman et al. "Clopidogrel, genetics, and drug responsiveness." New England journal of medicine, 2009, 360(4):411-413.

(Continued)

Primary Examiner — Heidi Reese
(74) Attorney, Agent, or Firm — Casimir Jones, S.C.

(57) ABSTRACT

This invention is in the field of medicinal chemistry. In particular, the invention relates to mixed disulfide conjugates of thienopyridine compounds, and their use as therapeutics for the treatment, amelioration, and prevention of cardiovascular diseases.

5 Claims, 9 Drawing Sheets

(56) References Cited

OTHER PUBLICATIONS

Gurbel and Tantry "Clopidogrel resistance?" Thromb Res, 2007, 120(3):311-321.
Hagihara et al. "Glutaredoxin and thiroedoxin can be involved in producing the pharmacologically active metabolite of a thienpyridine antiplatelet agent, prasugrel", 2011, Drug Metabolism and Disposition, 39 (2), pp. 208-214.
Hagihara et al. "Glutaredoxin is involved in the formation of the pharmacologically active metabolite of clopidogrel from its GSH conjugate." Drug Metab Dispos, 2012, 40(9):1854-1859.
International Search Report and Written Opinion, International Patent Application No. PCT/US2014/010348, mailed Apr. 7, 2014, thirteen pages.
Kazui et al. "Identification of the human cytochrome P450 enzymes involved in the two oxidative steps in the bioactivation of clopidogrel to its pharmacologically active metabolite." Drug Metab Dispos, 2010, 38(1):92-99.
Love et al. "Adverse haematological effects of ticlopidine. Prevention, recognition and management" Drug Saf., 1998, 19(2):89-98.
Lukesh et al. "A potent, versatile disulfide-reducing agent from aspartic acid." J Am Chem Soc, 2012, 134(9):4057-4059.
Mason et al. "Aspirin resistance and atherothrombotic disease." J Am Coll Cardiol, 2005, 46(6):986-993.
Mohan et al. "Identification and characterization of a principal oxidation impurity in clopidogrel drug substance and drug product." J Pharm Biomed Anal, 2008, 47(1):183-189.
Ono et al. "Agranulocytosis caused by ticlopidine and its mechanism." Am J Hematol, 1991, 37(4):239-242.
Pereillo et al. "Structure and stereochemistry of the active metabolite of clopidogrel." Drug Metab Dispos, 2002, 30(11):1288-1295.
Savi et al. "Identification and biological activity of the active metabolite of clopidogrel." Thromb Haemost, 2000, 84(5):891-896.
Shan et al. "Overcoming clopidogrel resistance: discovery of vicagrel as a highly potent and orally bioavailable antiplatelet agent" Journal of Medicinal Chemistry, 2012, vol. 55, No. 7, pp. 3342-3352.
Shuldiner et al. "Association of cytochrome P450 2C19 genotype with the antiplatelet effect and clinical efficacy of clopidogrel therapy." JAMA, 2009, 302(8):849-857.
Sofi et al. "Cytochrome P450 2C19*2 polymorphism and cardiovascular recurrences in patients taking clopidogrel: a meta-analysis." Pharmacogenomics J., 2011, 11(3):199-206.
Tuffal et al. "An improved method for specific and quantitative determination of the clopidogrel active metabolite isomers in human plasma." Thromb Haemost, 2011, 105(4):696-705.
Zhang et al. "Formation of the Thiol Conjugates and Active Metabolite of Clopidogrel by Human Liver Microsomes." Mol Pharmacol, 2012, 82(2):302-309.
Farid et al. "Metabolism and Disposition of the Thienopyridine Antiplatelet Drugs Ticlopidine, Clopidogrel, and Prasugrel in Humans" The Journal of Clinical Pharmacology, 2010, vol. 50, pp. 126-142.
KR Office Action mailed Nov. 24, 2016, KR Patent Application No. 10-2015-7019404, English translation provided.

* cited by examiner

Figure 5.
Figure 5A
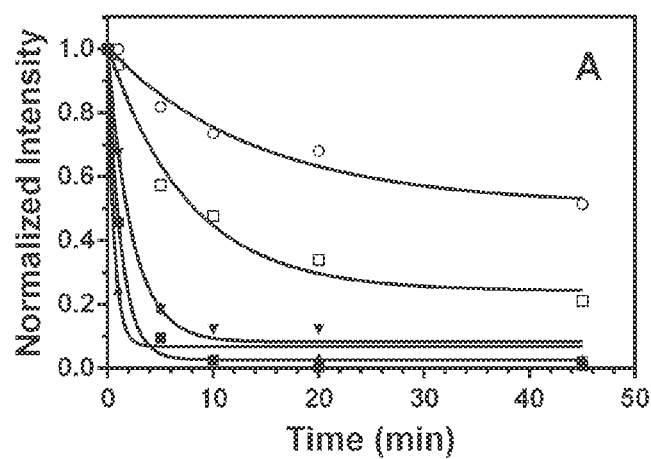
Figure 5B
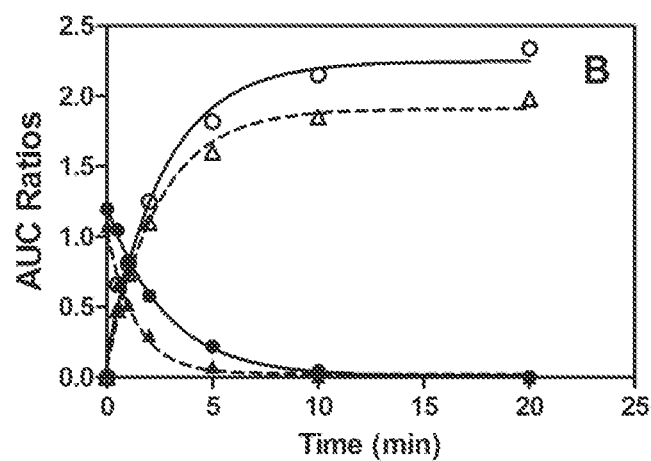

MIXED DISULFIDE CONJUGATES OF THIENOPYRIDINE COMPOUNDS AND USES THEREOF

STATEMENT REGARDING FEDERALLY SPONSORED RESEARCH OR DEVELOPMENT

This invention was made with government support under AA020090 and CA016954 awarded by the National Institutes of Health. The government has certain rights in the invention.

FIELD OF THE INVENTION

This invention is in the field of medicinal chemistry. In particular, the invention relates to mixed disulfide conjugates of thienopyridine compounds, and their use as therapeutics for the treatment, amelioration, and prevention of cardiovascular diseases.

INTRODUCTION

Thienopyridinyl compounds are widely used as antiplatelet agents to prevent heart attack and stroke. In this category, clopidogrel (Plavix), ticlopidine (Ticlid) and prasugrel (Effient) are three commonly used prodrugs. These agents require polymorphic cytochrome (P450) mediated oxidative bioactivation. Such oxidative bioactivation results in slow on-set of therapeutic effect and several adverse effects including neutropenia and thrombotic thrombocytopenic purpura.

Improved antiplatelet agents not requiring polymorphic cytochrome (P450) mediated oxidative bioactivation are needed.

SUMMARY OF THE INVENTION

Clopidogrel (Plavix), ticlopidine (Ticlid) and prasugrel (Effient) belong to a class of thienopyridinyl compounds widely used as antiplatelet agents to prevent heart attack and stroke. However, several serious drawbacks have been associated with these drugs including lack of response, toxicity and excessive bleeding. These drawbacks are closely related to the fact that they are all prodrugs that require oxidative bioactivation by polymorphic cytochromes P450 enzymes (P450s).

To overcome drawbacks associated with thienopyridine compounds (Clopidogrel (Plavix), ticlopidine (Ticlid) and prasugrel (Effient)), mixed disulfide conjugates of thienopyridine compounds were developed. Indeed, experiments conducted during the course of developing embodiments for the present invention demonstrated that the mixed disulfide conjugates of thienopyridine compounds of the present invention are capable of producing active thienopyridine metabolites (e.g., active thienopyridine metabolites capable of antiplatelet activity) in the presence of endogenous glutathione (GSH) without the need for bioactivation by P450s. This approach not only bypasses the oxidative bioactivation process by P450s, but circumvents many of the drawbacks associated with thienopyridinyl drugs. For example, the mixed disulfide conjugates of thienopyridine compounds of the present invention improve dosing consistency because production of the active metabolite from the conjugates is predictable. In addition, use of the mixed disulfide conjugates of thienopyridine compounds of the present invention as antiplatelet agents reduce the toxicity as toxic reactive metabolites are not produced by the thiol-exchange reaction.

In addition, the therapeutic onset time for the mixed disulfide conjugates of thienopyridine compounds of the present invention is shortened, which greatly benefits patients who experience acute cardiovascular events. For example, the standard regimen for thienopyridines requires continuously dosing patients for 3-5 days as only a small percentage of ingested thienopyridines are converted to the active metabolite. In contrast, the mixed disulfide conjugates of thienopyridine compounds of the present invention release the active metabolites with high yields in less than 30 min. In addition, the mixed disulfide conjugates of thienopyridine compounds of the present invention have superior stability over the active metabolites and therefore they can be used to quantitatively generate the active metabolites for basic and clinical research in vitro.

Accordingly, in certain embodiments, the present invention provides mixed disulfide conjugates of thienopyridine compounds capable of overcoming such drawbacks associated with thienopyridinyl compounds widely used as antiplatelet agents (e.g., Clopidogrel (Plavix), ticlopidine (Ticlid) and prasugrel (Effient)). The present invention is not limited to particular mixed disulfide conjugates of thienopyridine compounds. In some embodiments, the mixed disulfide conjugates of thienopyridine compounds are described by Formula I:

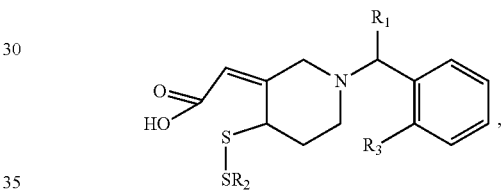

including pharmaceutically acceptable salts, solvates, and/or prodrugs thereof; wherein R1, R2, and R3 independently include any chemical moiety that renders the resulting compound capable of producing active thienopyridine metabolites upon interaction with endogenous glutathione (GSH) (e.g., active thienopyridine metabolites capable of antiplatelet activity).

In some embodiment, R is selected from the group consisting of H, —CO—OCH3, and

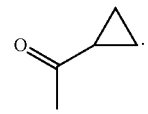

In some embodiments, R3 is Chlorine or Fluorine.

In some embodiments, R2 is selected from the group consisting of

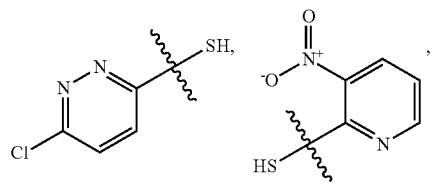

-continued

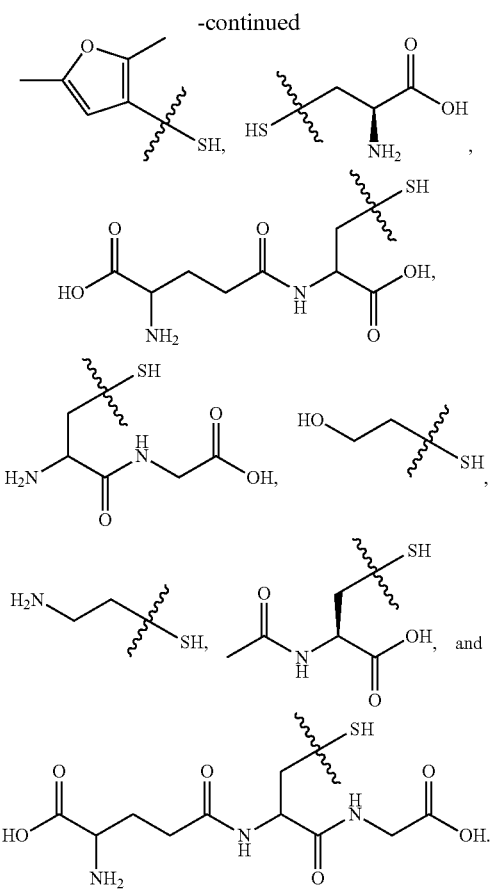

In certain embodiments, the present invention provides pharmaceutical compositions comprising a mixed disulfide conjugate of a thienopyridine compound and a pharmaceutically acceptable carrier.

In certain embodiments, the present invention provides pharmaceutical compositions comprising mixed disulfide conjugates of thienopyridine compounds configured for intravenous (IV) administration. In some embodiments, such pharmaceutical compositions comprising mixed disulfide conjugates of thienopyridine compounds configured for intravenous (IV) administration are used in the treatment, amelioration and prevention of atherothrombosis. In some embodiments, such pharmaceutical compositions comprising mixed disulfide conjugates of thienopyridine compounds configured for intravenous (IV) administration are used for rapid inhibition of platelet aggregation. In some embodiments, such pharmaceutical compositions comprising mixed disulfide conjugates of thienopyridine compounds configured for intravenous (IV) administration are used during percutaneous coronary intervention procedures (e.g., coronary angioplasty) for rapid inhibition of platelet aggregation.

In certain embodiments, the present invention provides methods of treating, ameliorating, or preventing a cardiovascular disease comprising administering to a patient a therapeutically effective amount of a mixed disulfide conjugate of a thienopyridine compound. In some embodiments, the administration is intravenous administration. In some embodiments, the cardiovascular disease is selected from the group consisting of coronary artery disease, peripheral vascular disease, and cerebrovascular disease. In some embodiments, the compound reduces aggregation of platelets (e.g., through irreversible binding to $P2Y_{12}$ receptors) (e.g., through blocking ADP receptors). In some embodiments, the compound is capable of producing active thienopyridine metabolites in the presence of endogenous glutathione without the need for bioactivation by P450s. In some embodiments, the methods further comprise co-administration of at least one agent selected from the group consisting of a HMG-CoA reductase inhibitor, an ACE Inhibitor, a Calcium Channel Blocker, a Platelet Aggregation Inhibitor, a Polyunsaturated Fatty Acid, Fibric Acid Derivative, a Bile Acid Sequestrant, an Antioxidant, and an Antianginal Agent.

In certain embodiments, the present invention provides methods of treating, ameliorating, or preventing aggregation of platelets onto blood vessels in a patient, comprising administering to the patient a therapeutically effective amount of a mixed disulfide conjugate of a thienopyridine compound. In some embodiments, the administration is intravenous administration. In some embodiments, the patient has or is at risk for developing cardiovascular disease (e.g., coronary artery disease, peripheral vascular disease, and cerebrovascular disease). In some embodiments, the treating, ameliorating, or preventing the aggregation of the platelets occurs through irreversible binding to $P2Y_{12}$ receptors. In some embodiments, the treating, ameliorating, or preventing the aggregation of the platelets occurs through blocking ADP receptors. In some embodiments, the mixed disulfide conjugate of thienopyridine compound is capable of producing active thienopyridine metabolites in the presence of endogenous glutathione without the need for bioactivation by P450s.

BRIEF DESCRIPTION OF DRAWINGS

FIG. 5 shows kinetics for the reduction of the mixed disulfide conjugates of clopidogrel by GSH. The mixed disulfide conjugates were prepared from the reaction mixtures containing 1 mg/ml HLM, 0.1 mM 2-oxoclopidogrel, the NADPH-regenerating system and various thiol reductants and purified using SPE C18 cartridges as described in Materials and Methods. The purified conjugates were then mixed with 1 mM GSH and 0.2 mg/ml cytosol (when present). The conjugate remaining and the AM formed were analyzed using LC-MS/MS. Legend: (A) reduction of the conjugates of BME (○), CPT (■), NAC (▼), DFT (▲), and NPT (□) by 1 mM GSH in the presence of 0.2 mg/ml cytosol. (B) reduction of the CPT conjugate by 1 mM GSH in the presence and absence of 0.2 mg/ml cytosol. Legend: (○), formation of AM in the absence of cytosol; (Δ), formation of the AM in the presence of cytosol; (●), reduction of the conjugate in the absence of cytosol; (▲), reduction of the conjugate in the presence of cytosol. The solid and dashed lines are non-linear curve fittings to a single exponential function.

DEFINITIONS

Figure 1:
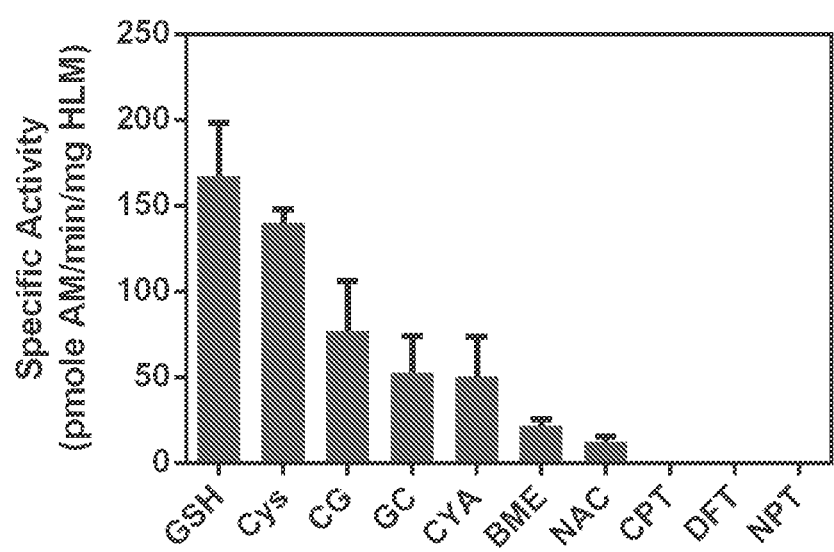
FIG. 1 shows effects of thiol reductants on the formation of the active metabolite (AM) of clopidogrel. The AM was produced in 0.1 ml of 50 mM KP buffer (pH 7.4) containing 0.2 mg/ml HLM, 0.1 mM 2-oxoclopidogrel, the NADPH-regenerating system, and the thiol reductants. The concentrations of the thiol reductants were 1 mM except for CPT, DFT and NPT which were 0.3 mM each. The reaction was initiated by the addition of 5 units of G6PD and incubated at 37° C. for 20 min. The active metabolite was then quantitated as the MP derivative as described in Materials and Methods. The reported rates were averaged over three separate measurements. Abbreviations for the thiol compounds are provided in Table 1.

The term "thienopyridine compound" as used herein, refers to a class of ADP receptor/P2Y12 inhibitors used for their anti-platelet activity. Examples include, but are not limited to, clopidogrel (Plavix), ticlopidine (Ticlid), and Prasugrel (Effient).

The term "mixed disulfide conjugate of a thienopyridine compound" as used herein, refers to a modified thienopyridine compound capable of producing active thienopyridine metabolites upon interaction with endogenous glutathione (GSH).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker. 1998; Methods in Enzymology, K. Widder et al. (eds.). Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment and/or prevention of platelet aggregation onto a blood vessel, in one embodiment, a therapeutically effective amount will refer to the amount of a therapeutic agent (e.g., a mixed disulfide conjugate of a thienopyridine compound) that decreases the reduces and/or prevents platelet aggregation by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Thienopyridinyl antiplatelet agents include three clinically used drugs, clopidogrel (Plavix), ticlopidine (Ticlid), and prasugrel (Effient). Their chemical structures and IUPAC names for clopidogrel (Plavix), ticlopidine (Ticlid), and prasugrel (Effient) are as follows:

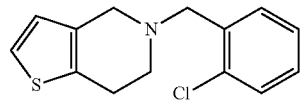

(ticlopidine; 5-(2-chlorobenzyl)-4,5,6,7-tetrahydrothieno[3,2c]pyridine),

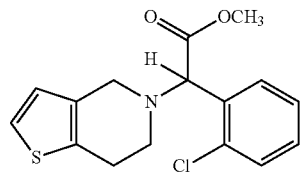 [SMILES: COC(=O)C(c1ccccc1Cl)N1CCc2sccc2C1]

(clopidogrel; (+)-(S)-methyl 2-(2-chlorophenyl)-2-(6,7-dihdrothieno[3,2-c]pyridine-5(4H)-yl)acetate), and

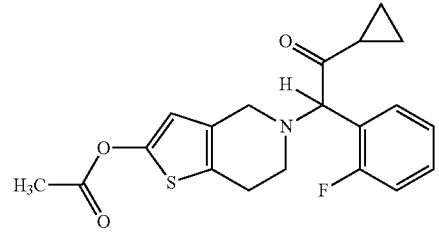 [SMILES: CC(=O)Oc1cc2c(s1)CCN(C(C(=O)C1CC1)c1ccccc1F)C2]

prasugrel; (RS)-5-[2-cyclopropyl-1-(2-fluorophenyl)-2-oxoethyl]-4,5,6,7-tetrahydrothieno[3,2-c]pyridine-2-yl acetate).

Thienopyridinyl antiplatelet agents are widely used to treat patients with acute cardiovascular syndromes and peripheral vascular diseases, particularly among those undergoing percutaneous coronary intervention (e.g., coronary angioplasty) to prevent heart attack and stroke. Nearly two million patients receive coronary and carotid stents every year in the United States and the annual sales for Plavix alone was worth $6.5 billion in 2010.

In spite of widespread use, clopidogrel has shown significant inter-individual variability in its efficacy (see, e.g., Freedman J E and Hylek E M (2009) New Engl J Med 360(4):411-413; Gurbel P A and Tantry U S (2007) Thromb Res 120(3):311-321; Sofi F, et al., (2011) Pharmacogenomics J 11(3):199-206). Nearly one-third of patients do not respond to clopidogrel therapy (see, e.g., Mason P J, Jacobs A K and Freedman J E (2005) J Am Coll Cardiol 46(6): 986-993). A large number of studies have been carried out attempting to identify genetic markers that correlate with the lack of response with the aim of overcoming this interindividual variability. It has been shown that clopidogrel is less effective in patients who carry the mutant CYP2C19*2 gene (see, e.g., Dick R J, Dear A E and Byron K A (2011) Heart Lung Circ 20(10):657-658; Shuldiner A R, et al., (2009) JAMA 302(8):849-857; Sofi F, et al., (2011) Pharmacogenomics J 11(3): 199-206). However the CYP2C19*2 mutant gene accounts for only 12% of the variations in response (see, e.g., Shuldiner A R, et al., (2009) JAMA 302(8):849-857). Other factors are likely involved, but have not been identified.

Indeed, though widely used as antiplatelet agents, there are drawbacks associated with thienopyridinyl antiplatelet agents. A major shortcoming for clopidogrel is a dosing inconsistency. For example, nearly one-third of patients do not respond to clopidogrel treatment. Ticlopidine can cause a series of adverse effects ranging from moderate symptoms of skin rashes and diarrhea to severe and sometimes fatal ones such as neutropenia and bone marrow aplasia. In rare cases it causes severe idiosyncratic events of agranulocytosis. Excessive bleeding has been associated with the use of prasugrel, particularly in older patients.

Such drawbacks associated with thienopyridinyl antiplatelet agents are closely related to the fact that these three drugs are all prodrugs that require oxidative bioactivation to the active metabolite (AM) by polymorphic cytochromes P450 (P450s) as illustrated in Scheme 1. Because of this oxidative bioactivation process, the amount of the active metabolite produced by P450s varies with the genetic makeup of each patient's hepatic P450s. Furthermore, these drugs are extensively metabolized by P450s to produce multiple metabolites, some of which are highly reactive and potentially toxic. It has been reported that the severe idiosyncratic events due to ticlopidine are associated with the production of reactive metabolites.

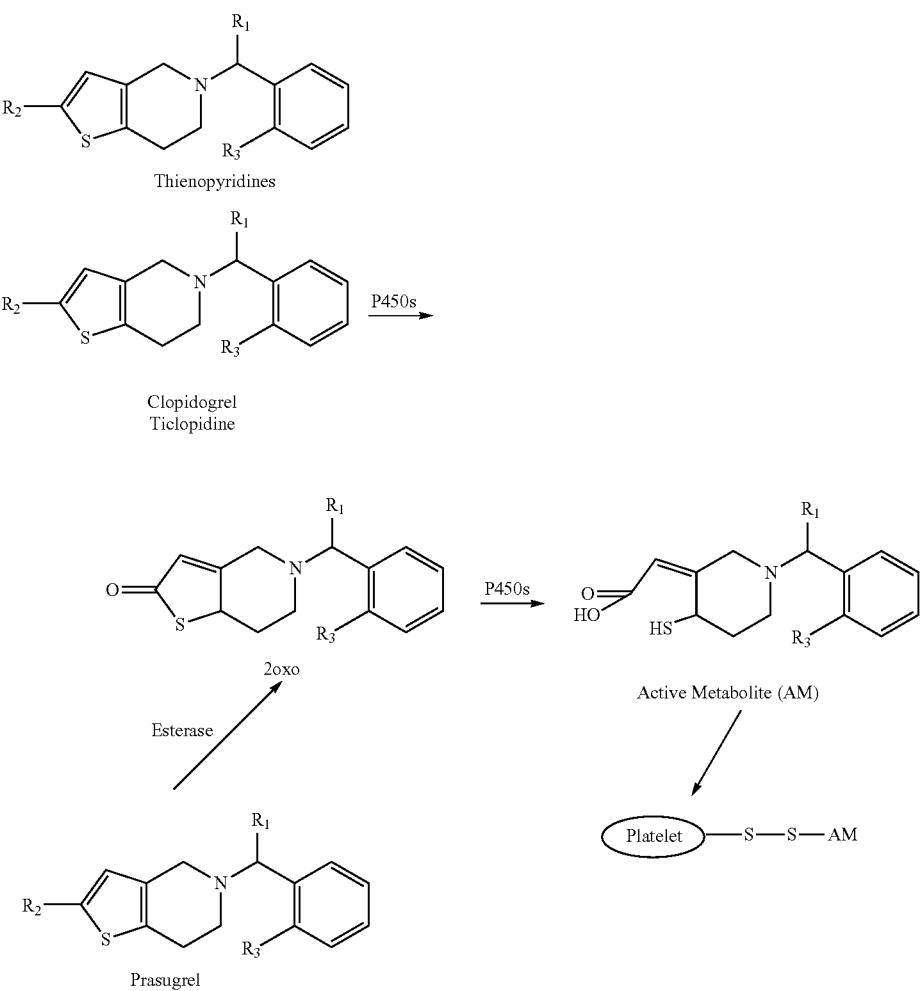

Scheme 1.

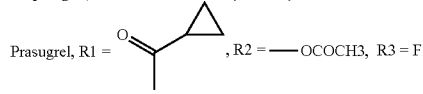

Ticlopidine, R1 = H, R2 = H, R3 = Cl
Clopidogrel, R1 = —CO—OCH3, R2 = H, R3 = Cl
Prasugrel, R1 = [structure], R2 = —OCOCH3, R3 = F As noted, the variable response to clopidogrel therapy is closely related to the fact that clopidogrel is a prodrug that requires oxidative bioactivation by cytochromes P450 (P450s) to its pharmacologically active metabolite (AM) (see. e.g., Kazui M, et al., (2010) Drug Metab Dispos 38(1):92-99; Savi P, et al., (2000) Thromb Haemost 84(5): 891-896). It is well documented that P450-mediated bioactivation involves two consecutive oxidative steps (see, e.g., Dansette P M, Thebault S, Bertho G and Mansuy D (2010) Chem Res Toxicol 23(7):1268-1274; Dansette P M, Rosi J, Bertho G and Mansuy D (2012) Chem Res Toxicol 25(2): 348-356); clopidogrel is first monooxygenated to 2-oxoclopidogrel, which is in turn oxidized to the AM in the second step. Although it has been argued that esterase PON1 is responsible for converting 2-oxoclopidogrel to the AM (see, e.g., Bouman H J, et al., (2011) Nat Med 17(1):110-116), increasing evidence supports the idea that 2-oxoclopidogrel is converted to the AM via a sulfenic acid intermediate (see. e.g., Dansette P M, Libraire J, Bertho G and Mansuy D (2009) Chem Res Toxicol 22(2):369-373; Dansette P M, Rosi J, Bertho G and Mansuy D (2012) Chem Res Toxicol 25(2):348-356; Dansette P M, Rosi J, Debernardi J, Bertho G and Mansuy D (2012) Chem Res Toxicol 25(5):1058-1065; Dansette P M, Thebault S, Bertho G and Mansuy D (2010) Chem Res Toxicol 23(7):1268-1274), as illustrated in Scheme 2.

responsible for inhibition of platelet aggregation through covalent modification of platelet P2Y$_{12}$ receptor (see, e.g., Ding Z, et al., (2003) Blood 101(10):3908-3914; Algaier I, et al., (2008) J Thromb Haemost 6(11):1908-1914). The anti-platelet activity of the mixed disulfide conjugate RS-SG remains untested.

Metabolism of 2-oxoclopidogrel in the presence of N-acetyl-L-cysteine (NAC) and L-cysteine leads to the formation of both the AM and mixed disulfide conjugates (see, e.g., Zhang H. Lau W C and Hollenberg P F (2012) Mol Pharmacol 82:302-309). In addition, it was demonstrated that the mixed disulfide conjugates of NAC and L-cysteine exchange thiols with GSH and that the equilibrium between the AM, the AM conjugate and GSH is governed by their redox potentials. The redox potential of the sulfenic acid intermediate is likely to be high because it is a reactive oxidant.

To overcome drawbacks associated with thienopyridine compounds, mixed disulfide conjugates of thienopyridine compounds were developed. Experiments conducted during the course of developing embodiments for the present invention demonstrated that the mixed disulfide conjugates of thienopyridine compounds of the present invention are capable of producing active metabolites in the presence of endogenous glutathione (GSH) without the need for bioactivation by P450s, as illustrated in Scheme 3. This approach

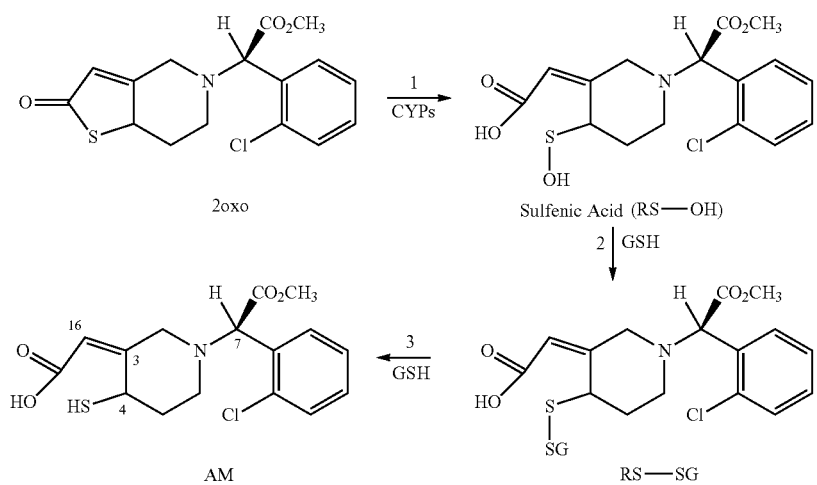

According to Scheme 2, 2-oxoclopidogrel is first oxidized to a sulfenic acid intermediate by P450s. The highly unstable sulfenic acid is then rapidly reduced by glutathione (GSH) to form a mixed disulfide conjugate (RS-SG) that is subsequently reduced by another GSH molecule to form the AM. This is consistent with the observation that GSH is required for the formation of the AM in human liver microsomes (HLMs) (see, e.g., Kazui M, et al., (2010) Drug Metab Dispos 38(1):92-99). It is widely accepted that the AM is not only bypasses the oxidative bioactivation process by P450s, but circumvents many of the drawbacks of the thienopyridinyl drugs. For example, the mixed disulfide conjugates of thienopyridine compounds of the present invention improve dosing consistency because production of the active metabolite from the conjugates is predictable. In addition, use of the mixed disulfide conjugates of thienopyridine compounds of the present invention as antiplatelet agents reduce the toxicity because toxic reactive metabolites are not produced by the thiol-exchange reaction. In addition, the therapeutic onset time for the mixed disulfide conjugates of thienopyridine compounds of the present invention will be shortened, which greatly benefits patients who experience acute cardiovascular events. The standard regimen for thienopyridines requires continuously dosing patients for 3-5 days because only a small percentage of ingested thienopyridines are converted to the active metabolite. In contrast the mixed disulfide conjugates of thienopyridine compounds of the present invention can release the active metabolites with high yields in less than 30 min. In addition, the mixed disulfide conjugates of thienopyridine compounds of the present invention have superior stability over the active metabolites and therefore they can be used to quantitatively generate the active metabolites for basic and clinical research in vitro.

Scheme 3.

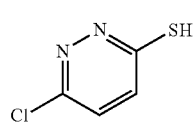

Within Scheme 3, examples of SR include, but are not limited to,

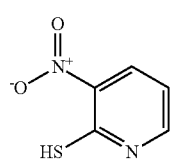

(6-chloropyridazine-3-thiol (CPT)),

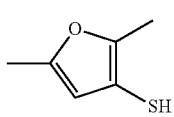

3-nitropyridine-2-thiol (NPT)),

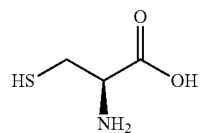

(2,5-dimethylfuran-3-thiol (DFT)),

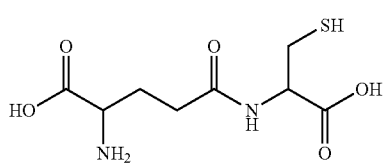 [SMILES: NC(CCC(=O)NC(CS)C(=O)O)C(=O)O]

(L-cysteine (CYS)), (g-L-glutamyl-L-cysteine (GC)),

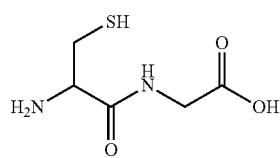 [SMILES: NC(CS)C(=O)NCC(=O)O]

(Cysteine-Glycine (CG)), (2-mercaptoethanol (BME)),

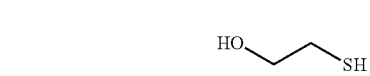

(cysteamine (CYA)), (N-acetyl-L-cysteine (NAC)), and

(glutathione (GSH)).

Accordingly, the present invention relates to mixed disulfide conjugates of thienopyridine compounds which are capable of producing active thienopyridine metabolites in the presence of endogenous glutathione (GSH) without the need for bioactivation by P450s. The invention further relates to methods of treating, ameliorating, or preventing cardiovascular disorders in a patient, such as those that are responsive to antiplatelet agents (such as clopidogrel, ticlopidine, and prasugrel) comprising administering to a patient a mixed disulfide conjugate of a thienopyridine compound of the invention. Such disorders include, but are not limited to, coronary artery disease, peripheral vascular disease, and cerebrovascular disease. In some embodiments, the mixed disulfide conjugates of thienopyridine compounds are used to inhibit platelet aggregation by, for example, altering the function of platelet membranes by blocking ADP receptors (e.g., thereby preventing a conformational change of glycoprotein IIb/IIIa which allows platelet binding to fibrinogen). In some embodiments, the mixed disulfide conjugates of thienopyridine compounds reduce aggregation ("clumping") of platelets by irreversibly binding to $P2Y_{12}$ receptors. In some embodiments, the mixed disulfide conjugates of thienopyridine compounds are used within pharmaceutical compostions configured for intravenous (IV) administration (e.g., in medical situations requiring IV administration of antiplate agents (e.g., coronary angioplasty)).

The present invention is not limited to particular mixed disulfide conjugates of thienopyridine compounds. In some embodiments, the mixed disulfide conjugates of thienopyridine compounds are described by Formula I:

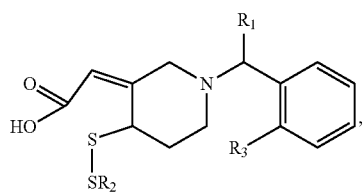

including pharmaceutically acceptable salts, solvates, and/or prodrugs thereof.

Formula I is not limited to a particular chemical moiety for R1, R2, and R3. In some embodiments, R1, R2, R3 each independently include any chemical moiety that renders the resulting compound capable of producing active thienopyridine metabolites in the presence of endogenous glutathione (GSH) without the need for bioactivation by P450s. In some embodiments, R1, R2, R3 each independently include any chemical moiety that renders the resulting compound capable of treating, ameliorating, or preventing cardiovascular disorders (e.g., coronary artery disease, peripheral vascular disease, and cerebrovascular disease) in a patient, such as those that are responsive to antiplatelet agents (such as clopidogrel, ticlopidine, and prasugrel). In some embodiments, R1, R2, R3 each independently include any chemical moiety that renders the resulting compound capable of inhibiting platelet aggregation by, for example, altering the function of platelet membranes by blocking ADP receptors (e.g., thereby preventing a conformational change of glycoprotein IIb/IIIa which allows platelet binding to fibrinogen). In some embodiments, R1, R2, R3 each independently include any chemical moiety that renders the resulting compound capable of reducing aggregation ("clumping") of platelets by irreversibly binding to $P2Y_{12}$ receptors.

In some embodiments, R1 is H, —CO—OCH3, or

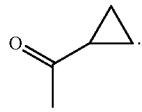

In some embodiments, R3 is Chlorine or Fluorine.

In some embodiments, R2 is selected from, but not limited to,

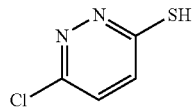

(6-chloropyridazine-3-thiol (CPT)),

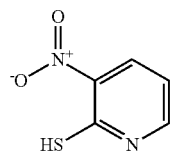

3-nitropyridine-2-thiol (NPT)),

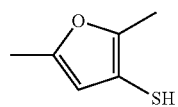

(2,5-dimethylfuran-3-thiol (DFT)),

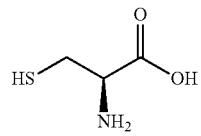

(L-cysteine (CYS)),

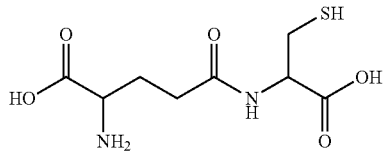 [SMILES: NC(CCC(=O)NC(CS)C(=O)O)C(=O)O]

(g-L-glutamyl-L-cysteine (GC)),

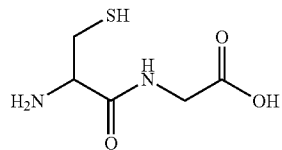

(Cysteine-Glycine (CG)),

(2-mercaptoethanol (BME)),

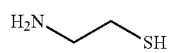
(cysteamine (CYA)),
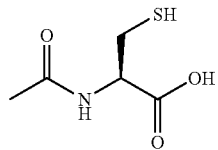
(N-acetyl-L-cysteine (NAC)), and
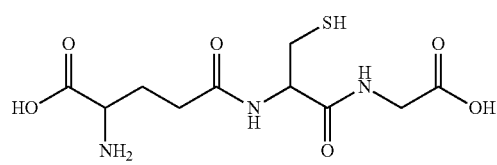 [SMILES: NC(CCC(=O)NC(CS)C(=O)NCC(=O)O)C(=O)O]
(glutathione (GSH)).
In some embodiments, the following mixed disulfide conjugates of thienopyridine compounds are contemplated for Formula I:
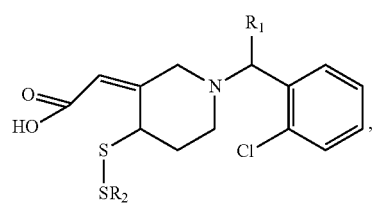
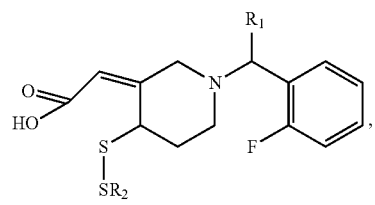
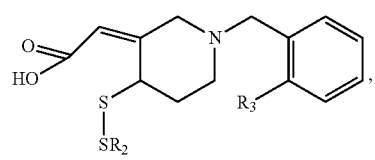
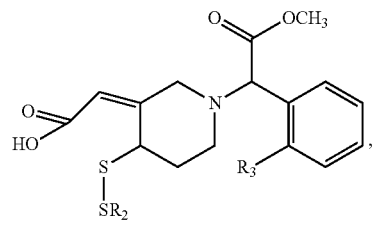
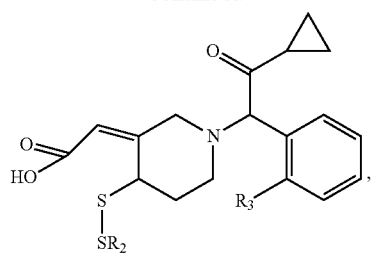
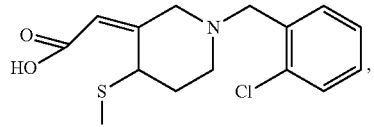
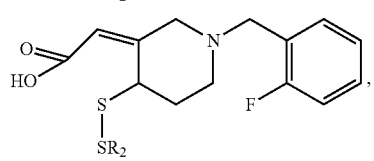
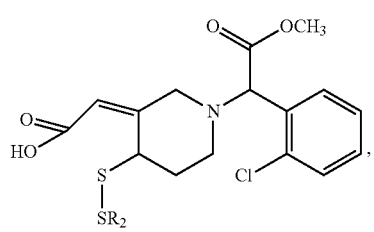
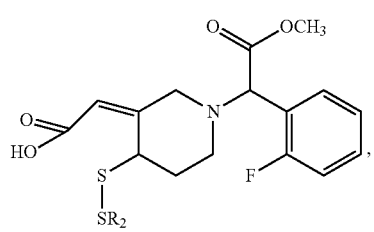
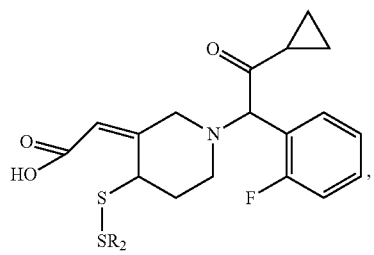
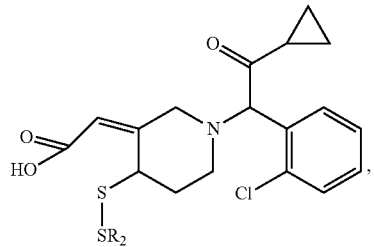

-continued
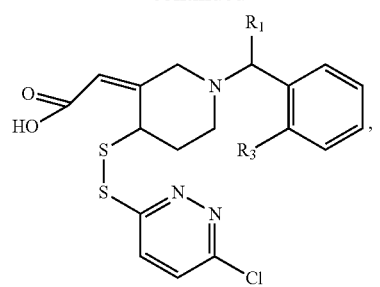
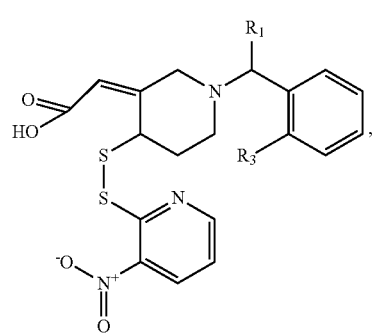
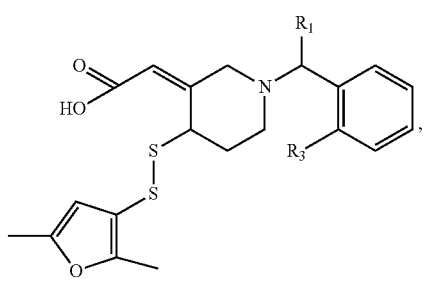
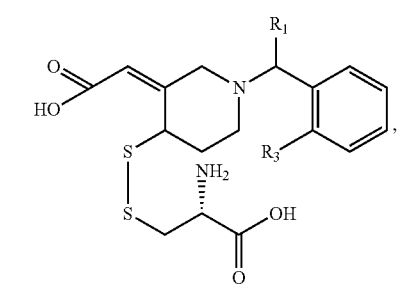
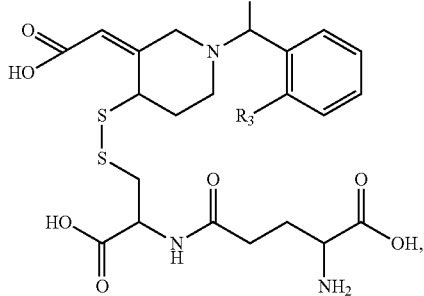
-continued
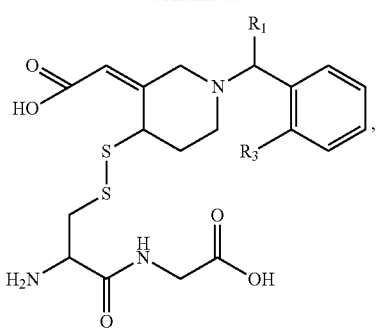
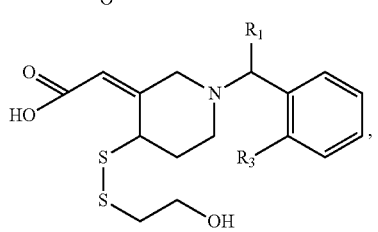
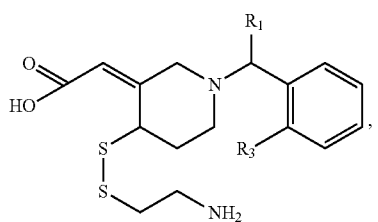
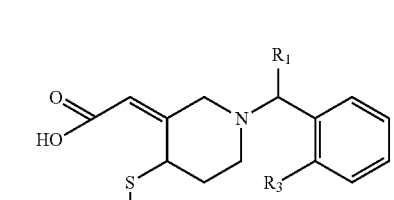
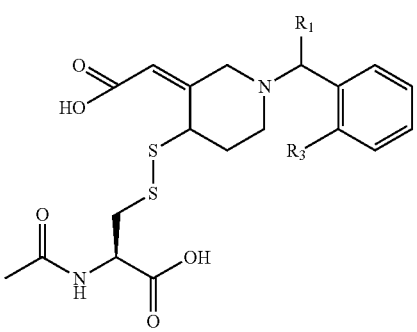
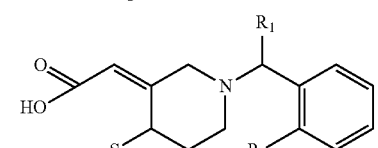
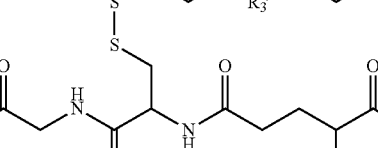
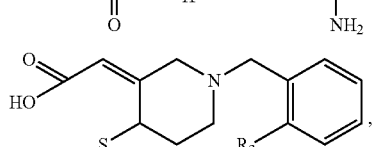
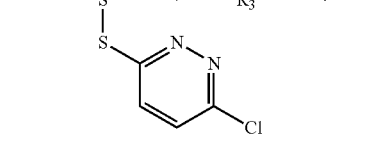

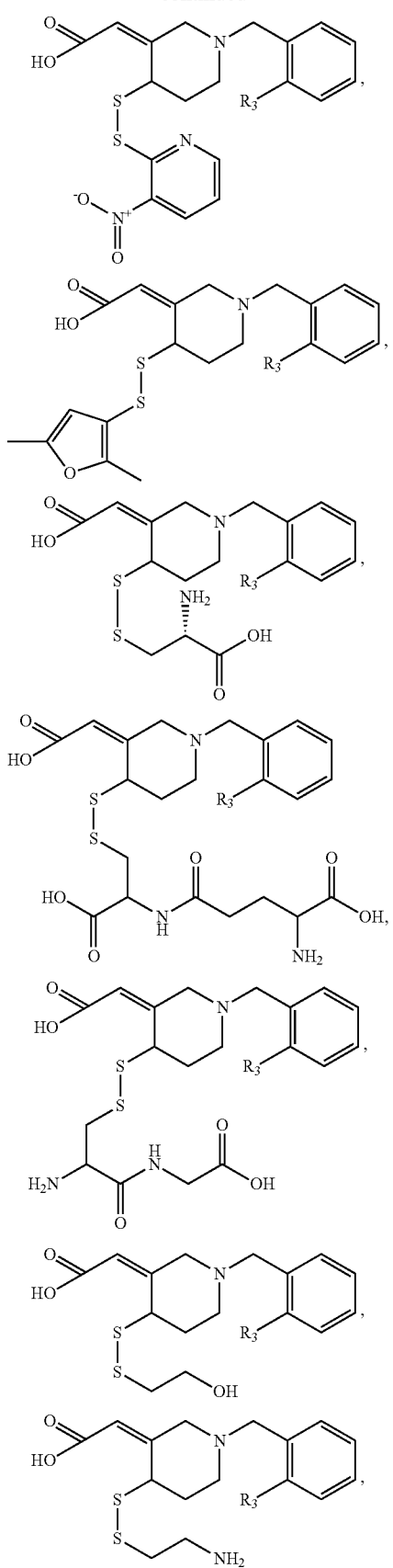
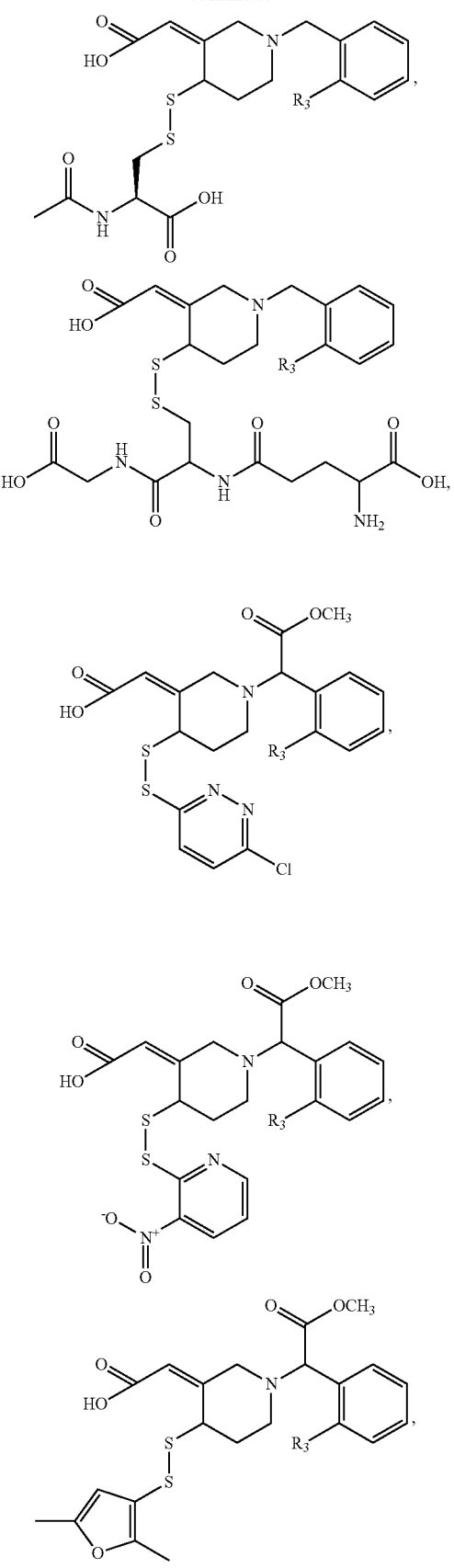

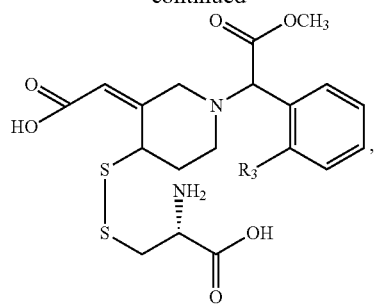
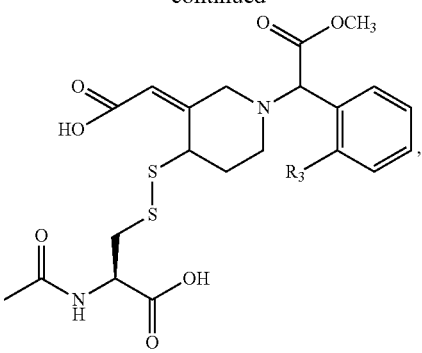
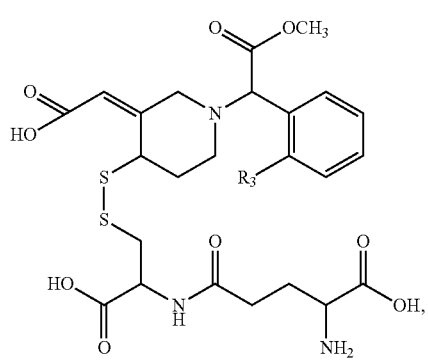
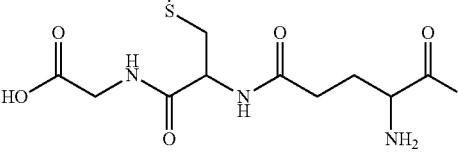
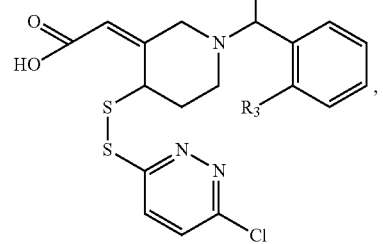
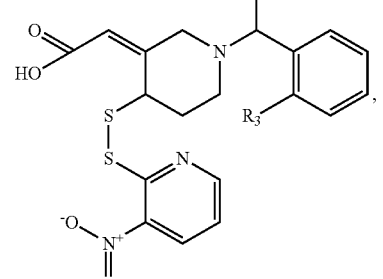
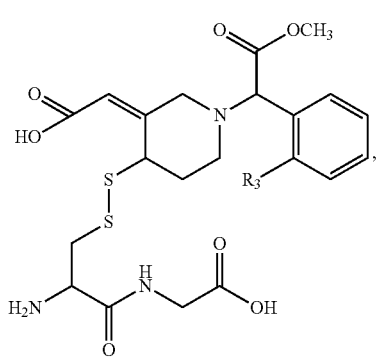
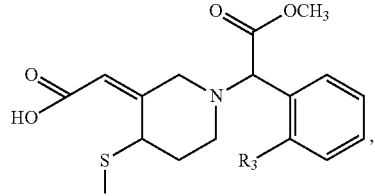
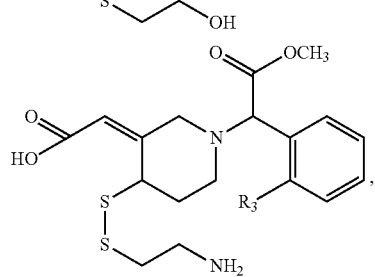

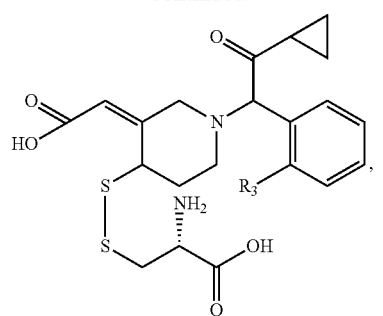
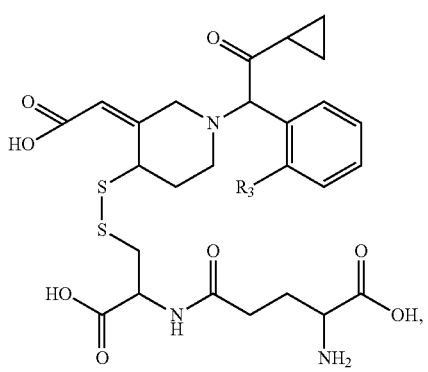
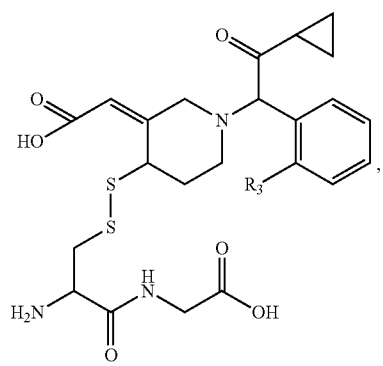
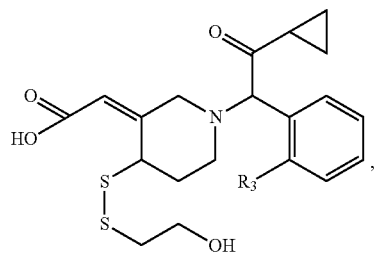
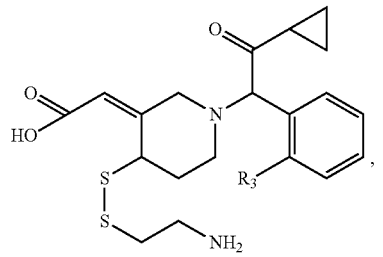
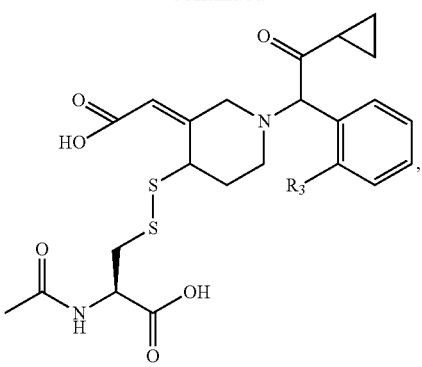
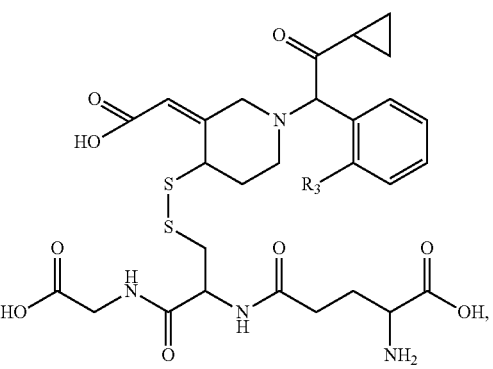
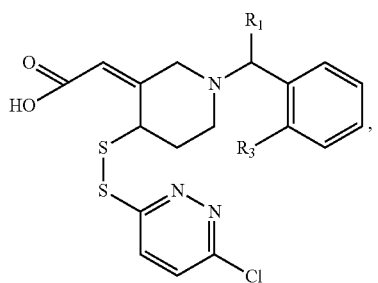
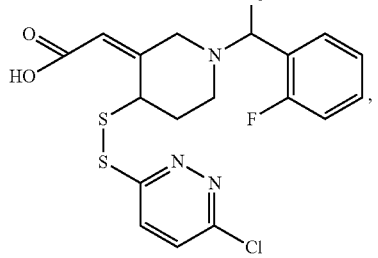
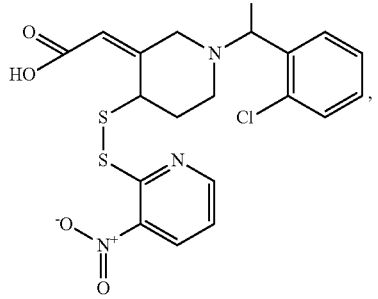

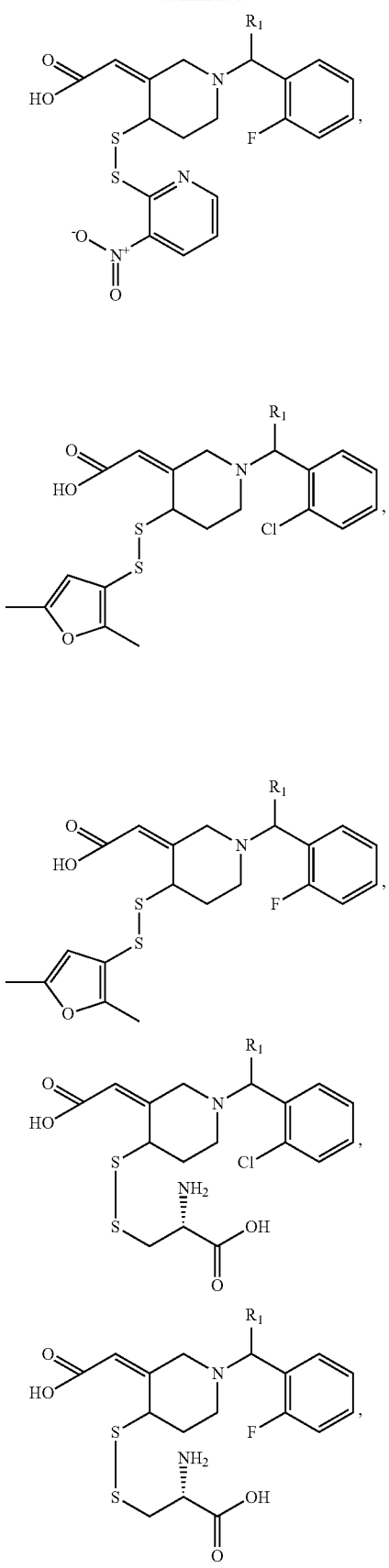
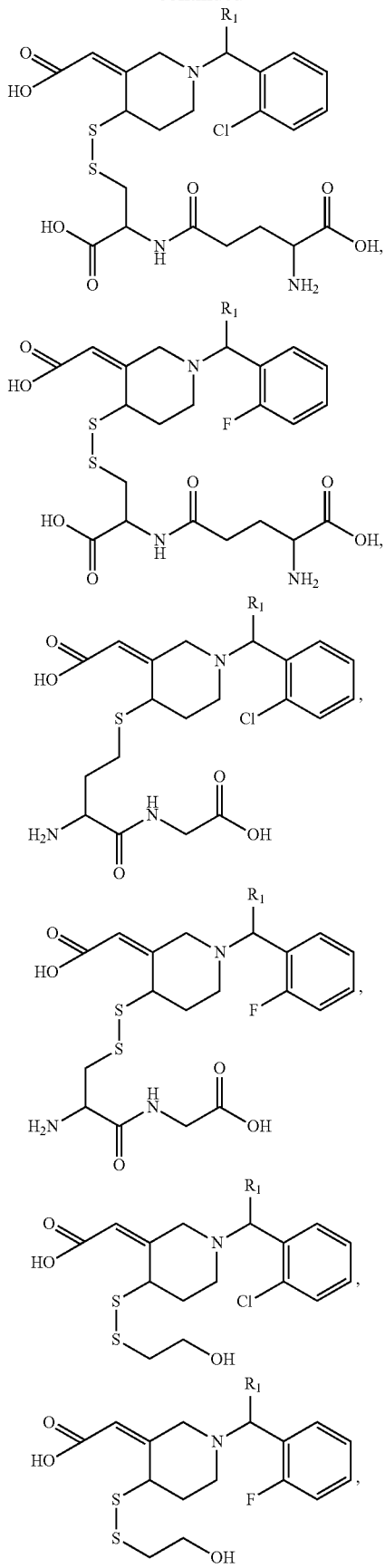

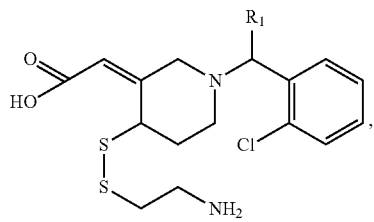
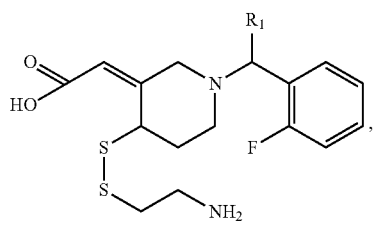
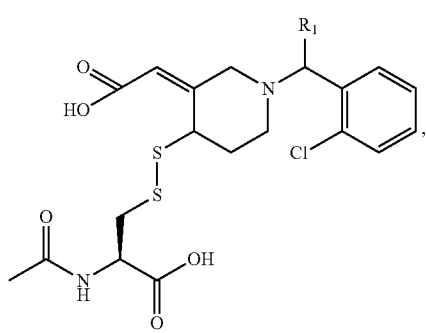
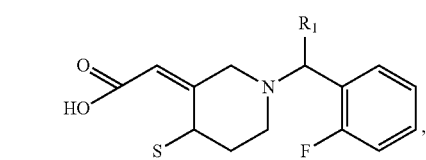
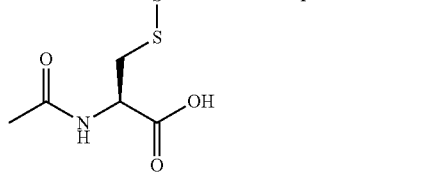
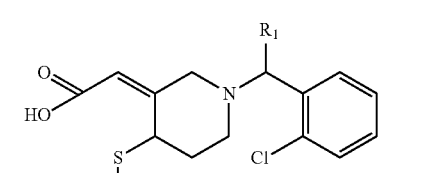
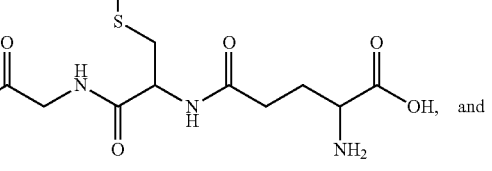
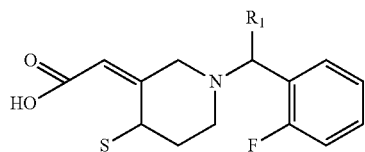
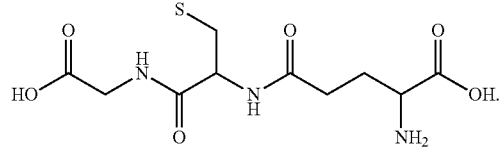
In some embodiments, the following mixed disulfide conjugates of thienopyridine compounds are contemplated for Formula I:
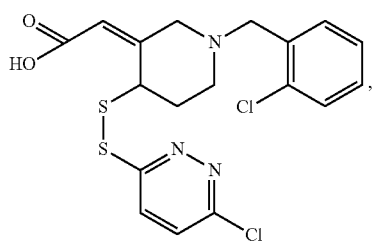
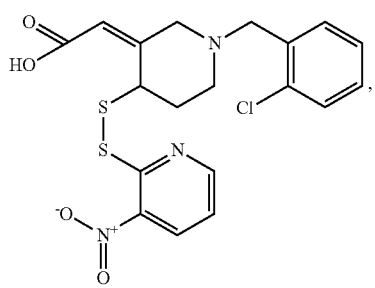
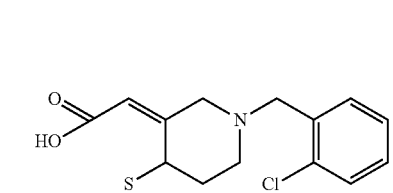
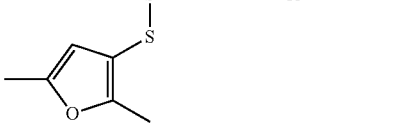
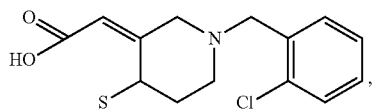
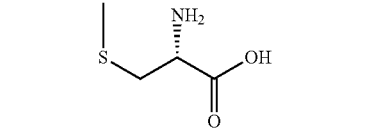

31
-continued
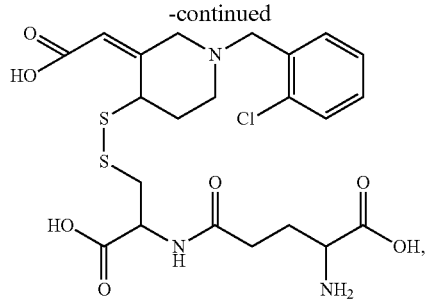
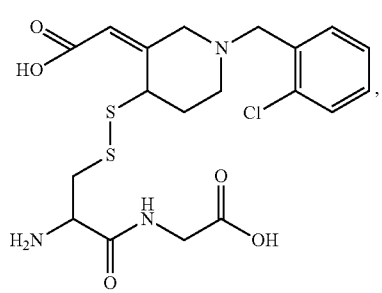
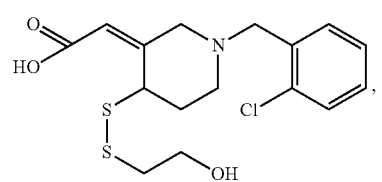
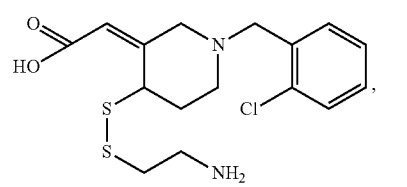
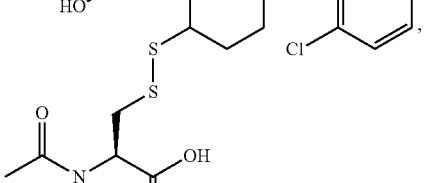
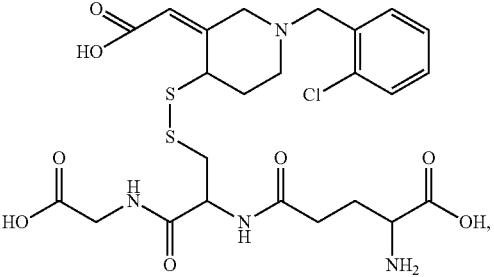
32
-continued
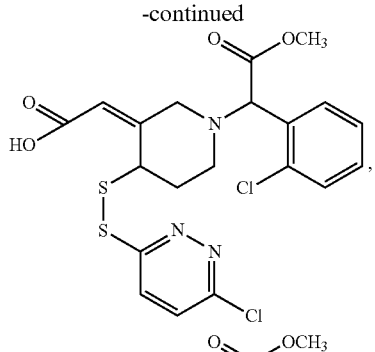
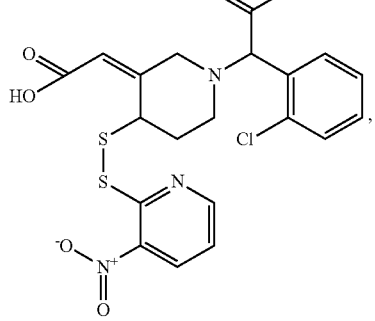
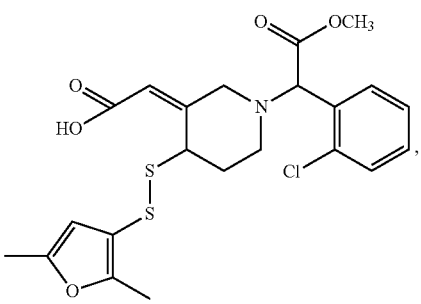
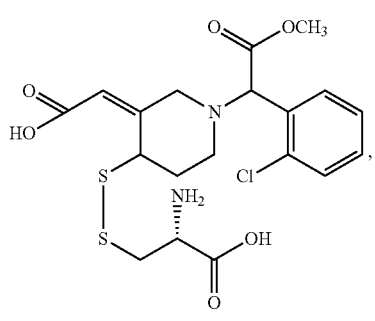
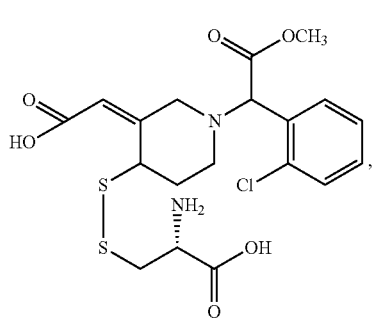
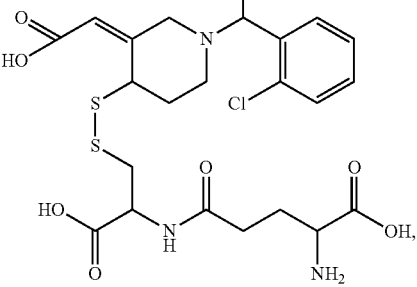

33
-continued
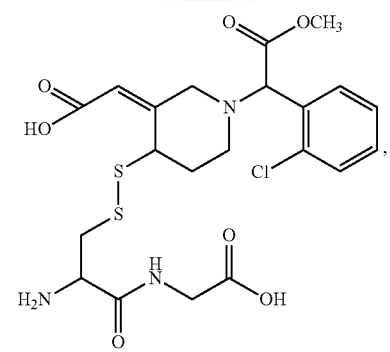
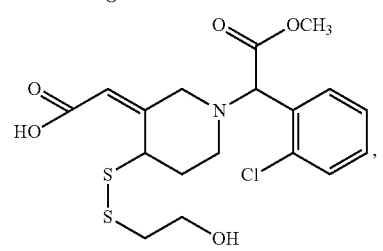
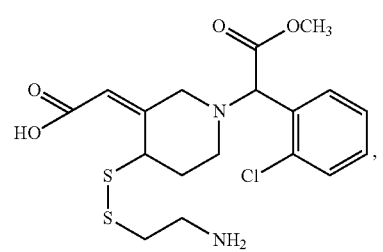
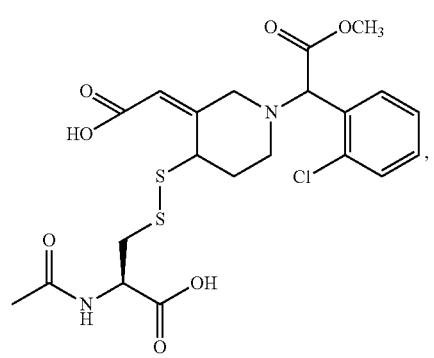
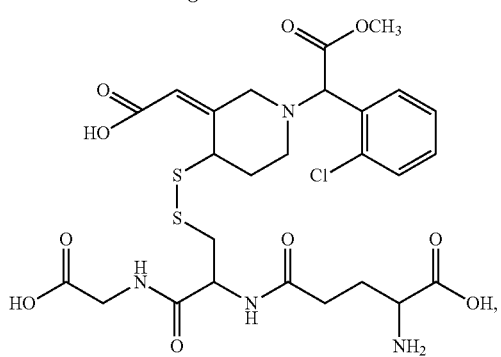
34
-continued
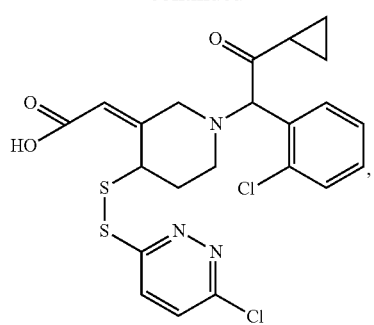
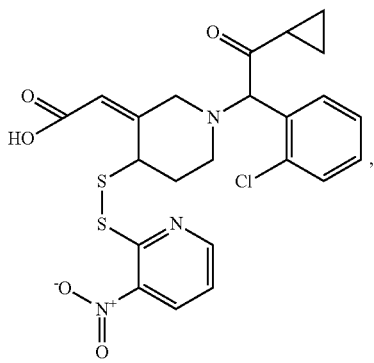
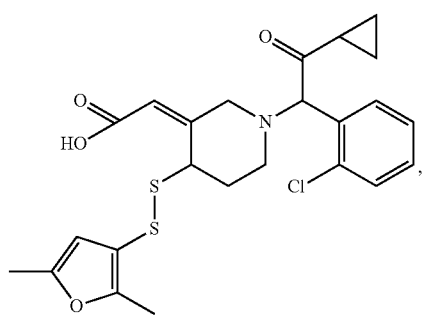
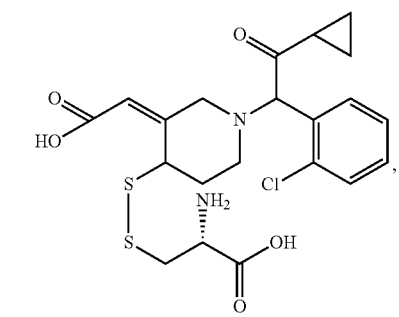
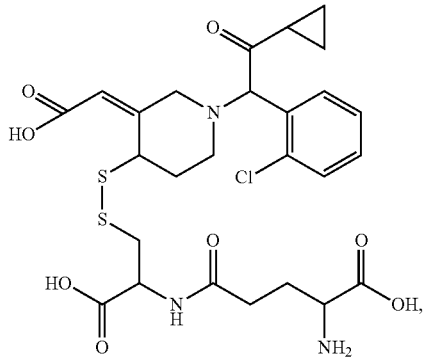

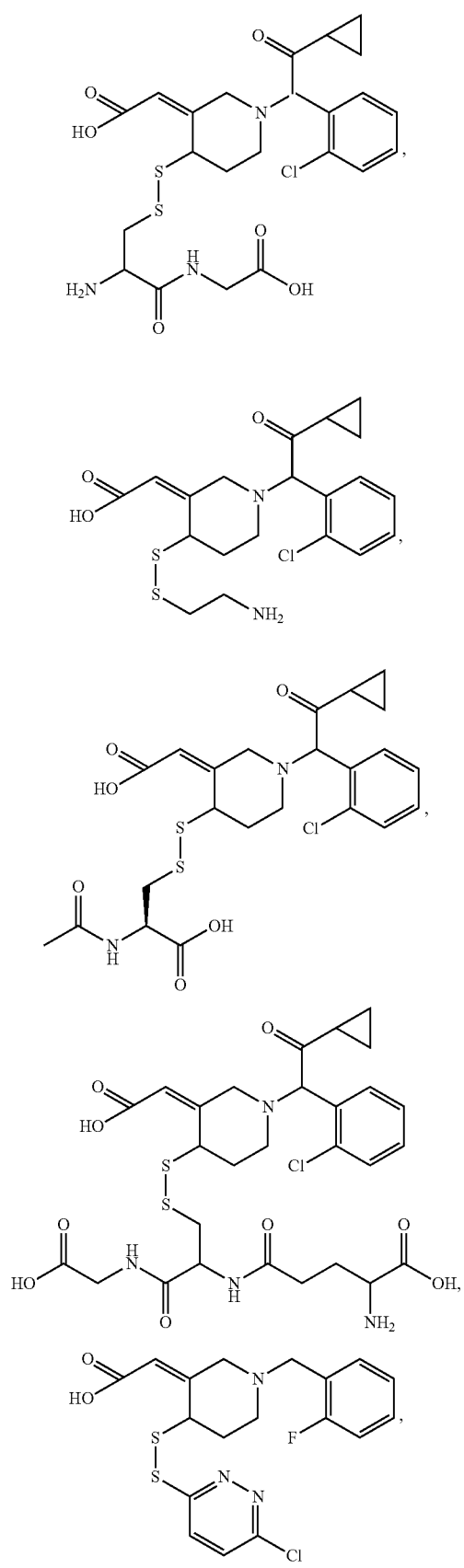
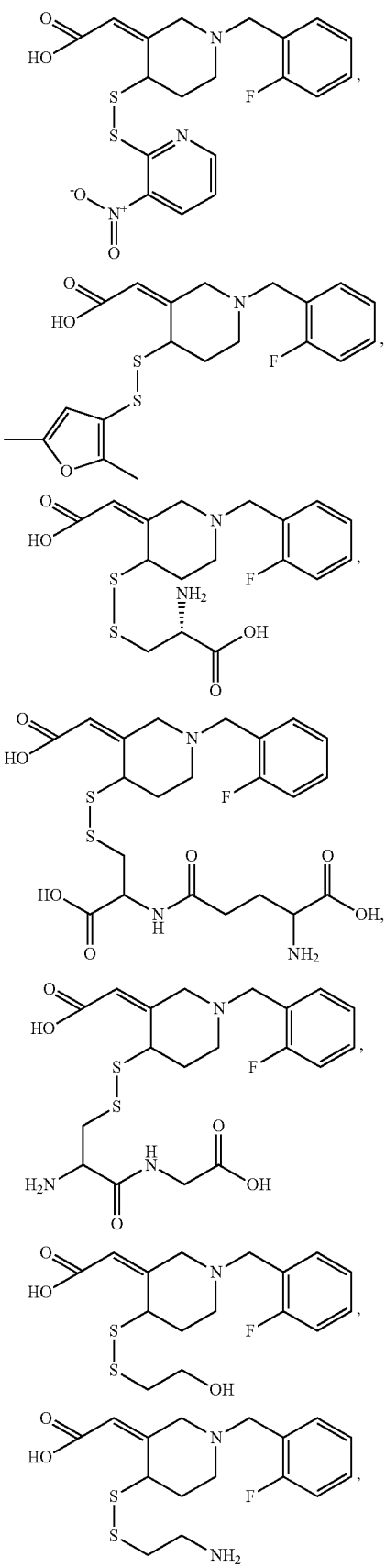

-continued
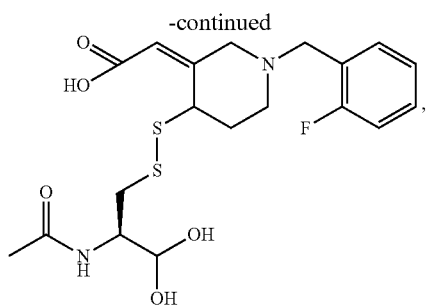
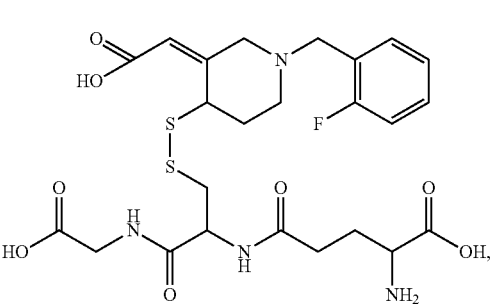
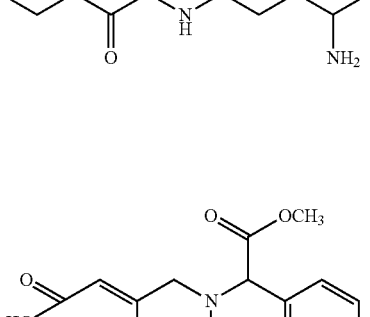
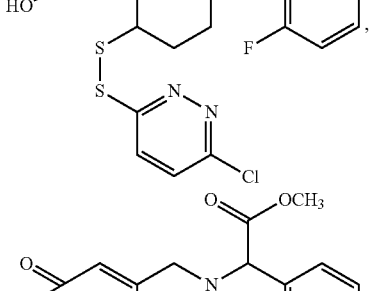
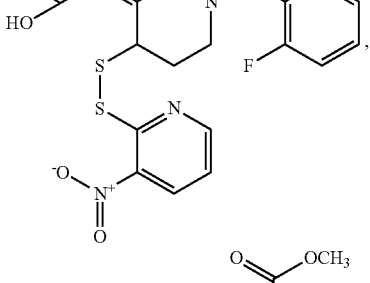
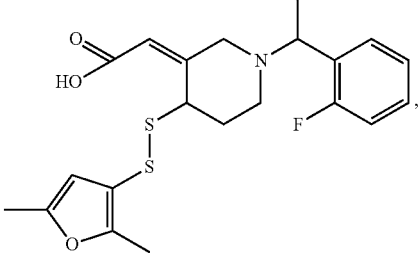
-continued
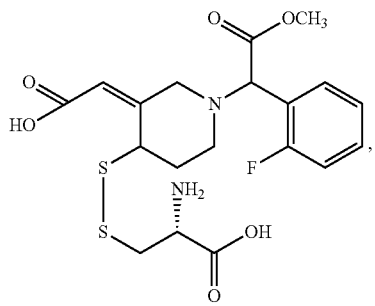
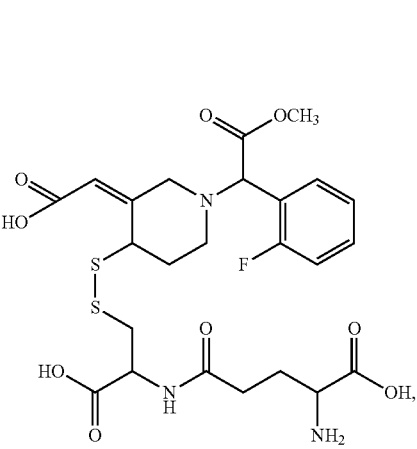
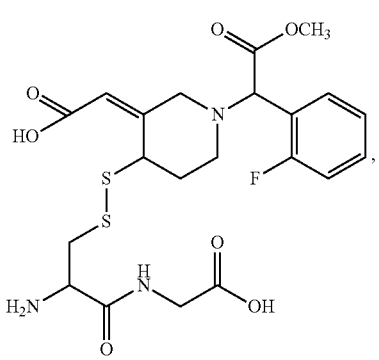
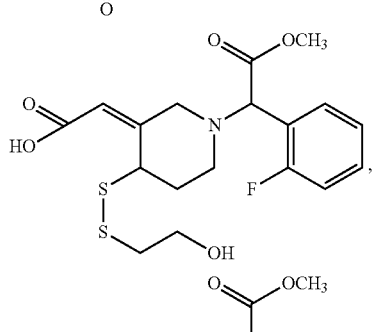
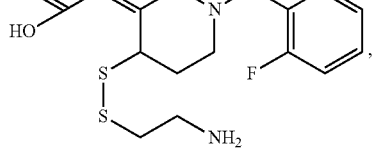

-continued
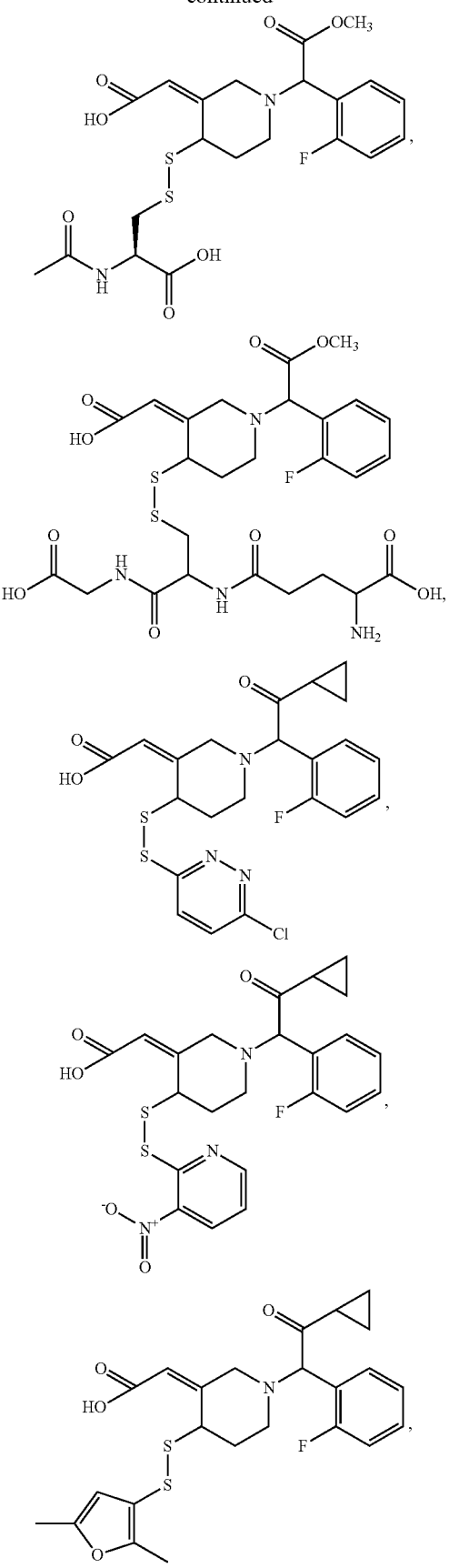
-continued
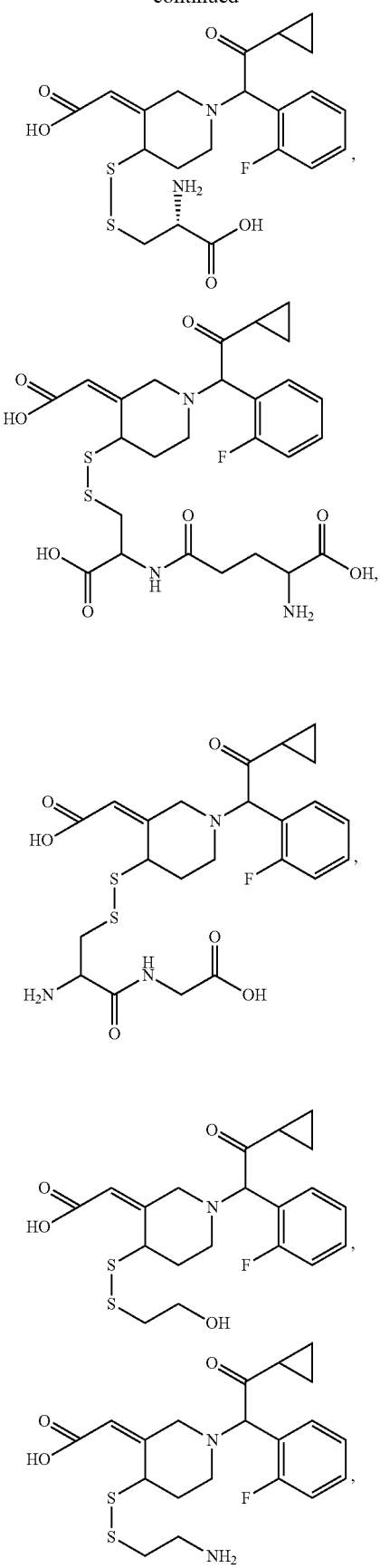

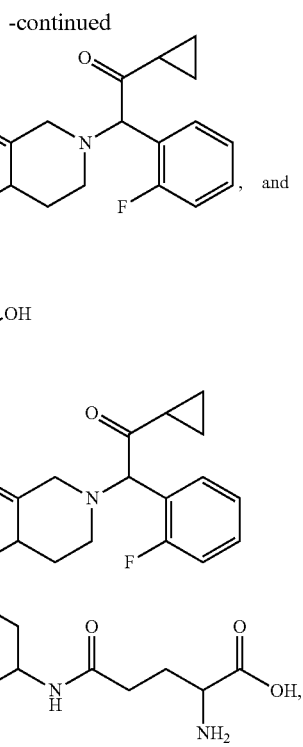

or a pharmaceutically acceptable salt, solvate, or prodrug thereof.

In some embodiments, the mixed disulfide conjugates of thienopyridine compounds are used to treat, ameliorate, or prevent cardiovascular disorders in an animal (e.g., a mammalian patient including, but not limited to, humans and veterinary animals), such as those that are responsive to antiplatelet agents (such as clopidogrel, ticlopidine, and prasugrel) comprising administering to a patient a mixed disulfide conjugate of thienopyridine compound of the invention. Such disorders include, but are not limited to, coronary artery disease, peripheral vascular disease, atherothrombosis, and cerebrovascular disease. Indeed, in some embodiments, the mixed disulfide conjugates of thienopyridine compounds are used to decrease platelet aggregation and/or inhibit thrombus formation. In this regard, such diseases and pathologies are amenable to treatment or prophylaxis using the present methods and mixed disulfide conjugates of thienopyridine compounds.

In some embodiments, the mixed disulfide conjugates of thienopyridine compounds are used in the prevention of vascular ischemic events in patients with symptomatic artherosclerosis. In some embodiments, the mixed disulfide conjugates of thienopyridine compounds are used to treat or prevent acute coronary syndrome without ST-segment elevation. In some embodiments, the mixed disulfide conjugates of thienopyridine compounds are used for the prevention of thrombosis after placement of intracoronary stent. In some embodiments, the mixed disulfide conjugates of thienopyridine compounds are used to inhibit platelet aggregation by, for example, altering the function of platelet membranes by blocking ADP receptors (e.g., thereby preventing a conformational change of glycoprotein IIb/IIIa which allows platelet binding to fibrinogen). In some embodiments, the mixed disulfide conjugates of thienopyridine compounds reduce aggregation ("clumping") of platelets by irreversibly binding to $P2Y_{12}$ receptors. In some embodiments, the mixed disulfide conjugates of thienopyridine compounds are used to prolong bleeding time. In some embodiments, the mixed disulfide conjugates of thienopyridine compounds are used to decrease incidence of stroke in high-risk patients.

In some embodiments, the present invention provides pharmaceutical compositions comprising mixed disulfide conjugates of thienopyridine compounds configured for intravenous (IV) administration. In some embodiments, such pharmaceutical compositions comprising mixed disulfide conjugates of thienopyridine compounds configured for intravenous (IV) administration are used in the treatment, amelioration and prevention of atherothrombosis. In some embodiments, such pharmaceutical compositions comprising mixed disulfide conjugates of thienopyridine compounds configured for intravenous (IV) administration are used for rapid inhibition of platelet aggregation. In some embodiments, such pharmaceutical compositions comprising mixed disulfide conjugates of thienopyridine compounds configured for intravenous (IV) administration are used during percutaneous coronary intervention procedures (e.g., coronary angioplasty) for rapid inhibition of platelet aggregation. Indeed, anti-platelet therapy is at the cornerstone of prevention and treatment of atherothrombosis. Platelet activation by agonists such as plaque rupture and sheer pressure stress from stents plays an important role in the development of atherothrombosis. Under certain clinical situations where patients suffer acute cardiovascular syndromes or undergo percutaneous cardiovascular intervention, rapid and complete inhibition of platelet aggregation is needed to prevent cardiovascular deaths and ischemic complications. Such medical scenarios require intravenous administration of anti-platelet agents that possess short onset time. However, this is still an unmet medical need since the anti-platelet agents currently being used either have slow onset time or cannot be administrated intravenously (see, e.g., Silvain, J., and Montalescot, G., (2012) Circ. Cariovasc. Interv. 5:328-331). The mixed disulfide conjugates of thienopyridine compounds of the present invention fulfill this unmet medical need as such compounds can be administrated both orally and intravenously and possess short onset time.

Some embodiments of the present invention provide methods for administering an effective amount of a mixed disulfide conjugate of a thienopyridine compound of the invention and at least one additional therapeutic agent (including, but not limited to, a therapeutic agent known to treat, ameliorate, or prevent cardiovascular disorders), and/or therapeutic technique (e.g., a surgical intervention). A number of therapeutic agents known to treat, ameliorate, or prevent cardiovascular disorders are contemplated for use in the methods of the present invention. Indeed, the present invention contemplates, but is not limited to, administration of numerous therapeutic agents known to treat, ameliorate, or prevent cardiovascular disorders. Examples include, but are not limited to, HMG-CoA reductase inhibitors (e.g., Atorvastatin (Lipitor), Pravastatin (Pravachol) Simvastatin (Zocor), Rosuvastatin (Crestor), Pitavastatin (Livalo), Lovastatin (Mevacor, Altocor), Fluvastatin (Lescol)), ACE Inhibitors (e.g., Ramipril (Altace), Quinapril (Accupril), Captopril (Capoten), Enalapril (Vasotec), Lisinopril (Zestril)). Calcium Channel Blockers (e.g., Amlodipine (Norvasc), Nifedipine (Procardia), Verapamil (Calan), Felodipine (Plendil), Diltiazem (Cardizem)), Platelet Aggregation Inhibitors (other than Ticlopidine, Clopidogrel, and Prasugrel) (e.g., Abciximab (ReoPro), Aspirin, Warfarin (Coumadin), Heparin), Polyunsaturated Fatty Acids (e.g., Omega-3 polyunsaturated fatty acid (Fish Oil)), Fibric Acid Derivatives (e.g., Fenofibrate (Tricor), Gemfibrozil (Lopid)), Bile Acid Sequestrants (e.g., Colestipol (Colestid), Cholestyramine (Questran)), Antioxidants (e.g., Vitamin E), Nicotinic Acid Derivatives (e.g., Niacin (Niaspan), Thromboytic agents (e.g., Alteplase (Activase)), and Antianginal Agents (e.g., Ranolazine (Ranexa).

In some embodiments of the present invention, a mixed disulfide conjugate of thienopyridine compound of the invention and one or more additional therapeutic agent is administered to an patient under one or more of the following conditions: at different periodicities, at different durations, at different concentrations, by different administration routes, etc. In some embodiments, the mixed disulfide conjugate of thienopyridine compound is administered prior to the additional therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the additional therapeutic agent. In some embodiments, the mixed disulfide conjugate of thienopyridine compound is administered after the additional therapeutic agent, e.g., 0.5, 1, 2, 3, 4, 5, 10, 12, or 18 hours, 1, 2, 3, 4, 5, or 6 days, or 1, 2, 3, or 4 weeks after the administration of the additional therapeutic agent. In some embodiments, the mixed disulfide conjugate of thienopyridine compound and the additional therapeutic agent are administered concurrently but on different schedules, e.g., the mixed disulfide conjugate of thienopyridine compound is administered daily while the additional therapeutic agent is administered once a week, once every two weeks, once every three weeks, or once every four weeks. In other embodiments, the mixed disulfide conjugate of thienopyridine compound is administered once a week while the additional therapeutic agent is administered daily, once a week, once every two weeks, once every three weeks, or once every four weeks.

Compositions within the scope of this invention include all compositions wherein the mixed disulfide conjugates of thienopyridine compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the mixed disulfide conjugate of thienopyridine compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the mixed disulfide conjugate of thienopyridine compound is present at a concentration of about 0.07-1.0 mg/ml, for example, about 0.1-0.5 mg/ml, and in one embodiment, about 0.4 mg/ml.

In addition to administering the mixed disulfide conjugate of thienopyridine compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the mixed disulfide conjugates of thienopyridine compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes the synthesis of mixed disulfide conjugates of clopidogrel and ticlopidine.

Synthesis of mixed disulfide conjugates of clopidogrel and ticlopidine was carried out in 50 mM potassium phosphate buffer using human liver microsomes (HLMs) according to Scheme 4.

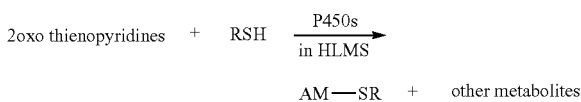

Scheme 4.

Within Scheme 4, RS (or —SR) are thiol-containing reagents selected from, but not limited to,

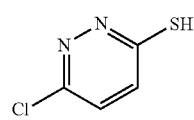

(6-chloropyridazine-3-thiol (CPT)),

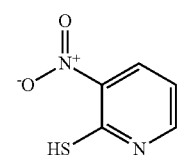

3-nitropyridine-2-thiol (NPT)),

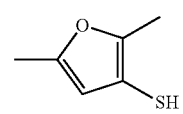

(2,5-dimethylfuran-3-thiol (DFT)),

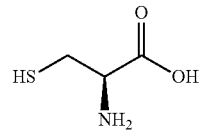

(L-cysteine (CYS)),

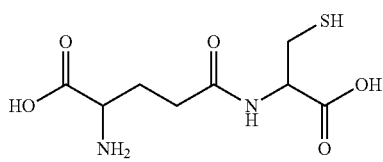 [SMILES: NC(CCC(=O)NC(CS)C(=O)O)C(=O)O]

(g-L-glutamyl-L-cysteine (GC)),

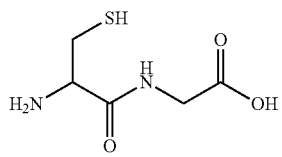

(Cysteine-Glycine (CG)),

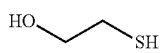

(2-mercaptoethanol BME)),

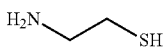

(cysteamine (CYA)),

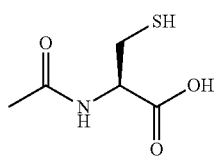

(N-acetyl-L-cysteine (NAC)), and

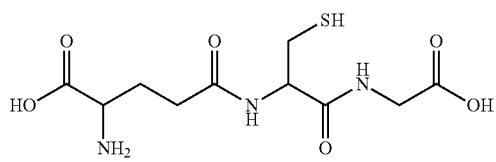 [SMILES: NC(CCC(=O)NC(CS)C(=O)NCC(=O)O)C(=O)O]

(glutathione (GSH)). Within Scheme 4, AM-SR represents a mixed disulfide conjugate of the present invention.

The results showed that all of the ten RS compounds formed the respective conjugates. In addition, it was confirmed that the reactant RS forms conjugate with the active metabolite through mixed disulfide bonds using tandem mass spectrometry. The conjugates were purified from the reaction mixtures using reverse phase chromatography.

Example II

This example describes production of the active metabolites from the mixed disulfide conjugate compounds.

The Conjugates Clop-CPT

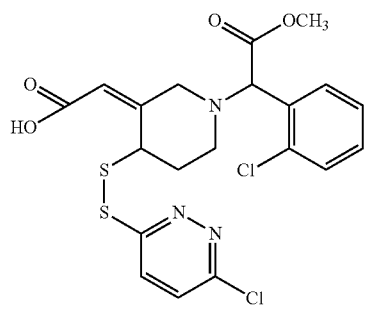

[(Z)-2-(1-(2-chlorophenyl)-2-methoxy-2-oxoethyl)-4-((6-chloropyridazin-3-yl)disulfanyl)piperidin-3-ylidene)acetic acid] and Tic-NPT

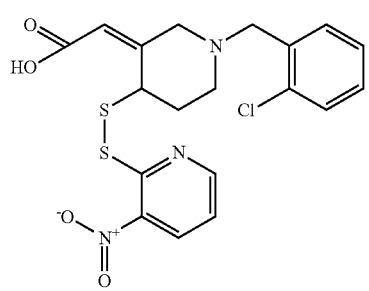

[(Z)-2-(1-(2-chlorobenzyl)-4-((3-nitropyridin-2-yl)disulfanyl)piperidin-3-ylidene)acetic acid] were chosen for further studies.

The ability of the mixed disulfide conjugate Clop-CPT and Tic-NPT to produce the active metabolites (AM) in the presence of glutathione was next tested. Clop-CPT was rapidly reduced by 1 mM GSH with a concomitant increase in the amount of the AM of clopidogrel. The half-life for the production of the AM of clopidogrel from the clop-CPT conjugate was only 1.8 min. The same is true for tic-NPT conjugate, but the half-life was 14.7 min.

Example III

This example describes inhibition of platelet aggregation by mixed disulfide conjugates of thienopyridine compounds of the present invention.

To demonstrate the mixed disulfide conjugates of thienopyridine compounds of the present invention are capable of inhibiting platelet aggregation in the presence of GSH, platelet aggregation assays were conducted. Approximately 20 ml blood was drawn from rabbits and platelets were collected by centrifugation whereas the supernatants were collected as platelet poor plasma (PPP). Prior to the inhibition assay, the conjugates of Clop-CPT and Tic-NPT were dissolved in 0.5 ml PPP and incubated with 1 mM GSH at 37° C. for 30 min to produce the active metabolite. The platelets were then re-suspended gently in the PPP containing the active metabolite. After incubation at 37° C. for one hour, platelet aggregation was initiated by the addition of 5 µM of the agonist ADP. Platelet aggregation was then recorded using an aggregometer.

Conjugates of Clop-CPT and Tic-NPT inhibited platelet aggregation by approximately 60% in the presence of 1 mM GSH compared with the negative control that contained no conjugate. This level of inhibition was approximately the same as the positive control that contained the active metabolite generated from human liver microsomes (HLMs).

Example IV

This example describes the materials and methods for Examples 5-9.

Chemicals.

(S)-clopidogrel, racemic 2-oxoclopidogrel, and cis-clopidogrel-MP were purchased from Toronto Research Company (Ontario, Canada). Glutathione (GSH), γ-L-glutamyl-L-cysteine (GC), Cys-Gly (CG), L-cysteine, β-mercaptoethanol (BME), N-acetyl-L-cysteine (NAC), cysteamine (CYA) hydrochloride, 2,5-dimethylfuran-3-thiol, 6-chloropyridazine-3-thiol, 3-nitropyridine-2-thiol, and 2-bromo-3'-methoxyacetophenone (MPB) were purchased from Sigma-Aldrich company (St. Louis, Mo.). Pooled HLMs and cytosol were purchased from XenoTech (Lenexa, Kans.).

Determination of the Rate for the Formation of the AM by HLMs in the Presence of Various Thiol Reductants.

To examine the effects of various thiol reductants on the formation of the active metabolite (AM), the rates at which the AM was produced were determined. Production of the AM was performed in 0.1 ml of 50 mM potassium phosphate (KPi) buffer (pH 7.4) containing 0.2 mg/mL HLM, 0.1 mM 2-oxoclopidogrel, the NADPH-regenerating system, and 1 mM of each of the thiol reductants except that 0.3 mM CPT, DFT, or NPT were used. The reaction was initiated by the addition of 5 units of glucose-6-phosphate dehydrogenase (G6PD) and incubated at 37° C. for 20 min. The AM was then derivatized with 4 mM MPB at room temperature for 10 min, followed by acidification with acetic acid to 3% (v/v). For quantification, 50 pmoles of (S)-clopidogrel was added into each reaction mixture as internal standard (1S). The derivatized AM (AM-MP) was quantitated using LC-MS/MS.

The MS analyses of the reaction mixture were performed on an ion-trap mass spectrometer (LCQ DecaXP, Thermo Fisher Scientific, Waltham, Mass.) as reported previously (Zhang et al., 2012). In brief, the metabolites of 2-oxoclopidogrel were separated on a reverse phase C18 column (2×100 mm, 3 µm, Phenemonex, CA) using a binary mobile phase at a flow rate of 0.2 ml/min. The temperature of the C18 column was maintained at 40° C. using a column heater (Restek Corporation, Lancaster, Pa.). The mass spectrometer was operated in positive electrospray ionization mode with the following settings: heated capillary temperature, 200° C.; Spray voltage, +4.5 kV; sheath gas flow, 60 (arbitrary units); auxiliary gas, 20 (arbitrary units). The AM-MP and IS were fragmented in the MS through collision-induced dissociation (CID) at 35% energy level. Transitions from m/z 504→m/z 354 for the AM-MP and from m/z 322→m/z 212 for the IS were used to quantitate the amount of the AM-MP based on a calibration curve consisting of various concentrations of cis-clopidogrel-MP.

Analyses of the Mixed Disulfide Conjugates of Clopidogrel Using LC-MS/MS.

The mixed disulfide conjugates were produced by HLMs for both structural and semi-quantitative analyses. Metabolism of 2-oxoclopidogrel was performed in 0.2 ml of 50 mM KP buffer (pH 7.4) as described above except that the concentration of HLMs was increased to 1 mg/ml. The reaction was incubated at 37° C. for 30 min and then quenched by the addition of 0.1 ml of 10% of acetic acid in acetonitrile. The quenched samples were centrifuged at 13,000×g for 10 min to remove the HLMs. Aliquots of 50 µl of the supernatant were loaded onto a mass spectrometer to analyze both the active and conjugate metabolites.

The MS analyses were performed as described above except that the MS detector was operated in the dependent scan mode. The precursor ions were scanned from m/z 300-700, whereas the $MS^2$ spectra were obtained from m/z 100 to 700 for the four most abundant ions. For semi-quantitative analysis, 50 pmoles of the IS was spiked into each sample that had been quenched. The relative amounts of the AM and respective conjugates were calculated as the AUC ratios of the metabolites to that of the IS.

Determination of the Kinetics for the Conversion of the Mixed Disulfide Conjugates to the AM.

To examine the reactivity of the mixed disulfide conjugates, the kinetics for the reduction of the mixed disulfide conjugates by GSH were determined. The mixed disulfide conjugates were generated in 1 ml of 50 mM KPi buffer (pH 7.4) buffer containing 1 mg/ml HLM, 0.1 mM 2-oxoclopidogrel and 0.3 or 1 mM thiol reductants. The reaction was incubated at 37° C. for 50 min after initiated by the addition of G6PD. The reaction mixture was then centrifuged at 13,000×g to remove the HLMs and the supernatant was loaded to a pre-conditioned SPE cartridge (C18, 100 mg/1 ml, Agilent Technologies, CA) and the mixed disulfide conjugate was eluted with 2 ml of methanol. The eluent was then dried using a Speedvac concentrator and the dried sample was stored at −80° C. until use. Prior to the kinetic measurements, the dried samples were first re-dissolved in 0.5 ml of 50 mM KPi buffer (pH 7.4) and then equilibrated at 37° C. for 5 min. Small aliquots (1-5 µl) of stock GSH and cytosol (when present) solutions were added to the conjugate samples at 1 mM and 0.2 mg/ml, respectively, to initiate the thiol-disulfide exchange reaction. At designated times, an aliquot of 50 µl of the reaction mixture was withdrawn and mixed with 25 µl of 10% acetic acid in acetonitrile to terminate the thiol-disulfide exchange reaction. The t=0 sample was prepared immediately prior to the addition of GSH. The amounts of the mixed disulfide conjugates and the AM were analyzed using LC-MS/MS as described above.

Formation of Active Metabolite H4 from the Mixed Disulfide Conjugates of Clopidogrel.

Since the anti-platelet activity of the AM is closely related to its stereochemistry, the stereochemistry of the mixed disulfide conjugates formed in the presence of CPT. DFT or NPT was investigated because of their relatively high redox potentials. Due to lack of genuine standards for the stereoisomers of the AM, the mixed disulfide conjugates with GSH were first treated to release the AM and then derivatized the AM with MPB so as to compare the AM-MP derivatives with the cis-clopidogrel-MP standard. Preparation and reduction of the conjugates with GSH were performed as described above. After an incubation of 20 min at 37° C. with 1 mM GSH, MPB was added at 4 mM to alkylate the AM. The alkylation reaction was terminated in 10 min by the addition of half a volume of 10% acetic acid in acetonitrile. An aliquot of 50 µl of the reaction mixture was subjected to LC-MS/MS analysis as described for the quantitation of the AM.

Anti-Platelet Activity of the Mixed Disulfide Conjugates of Clopidogrel.

In order to generate sufficient quantities of the mixed disulfide conjugates, the metabolism of 2-oxoclopidogrel was performed in 2-ml reaction mixtures containing 1 mg/ml HLM, 0.1 mM 2-oxoclopidogrel, the NADPH-regenerating system, and 0.3 mM CPT or NPT or 1 mM GSH. The reaction was initiated by the addition of 10 units G6PD and incubated at 37° C. for 50 min. Two control samples were prepared in parallel. One control sample did not contain any G6PD (-G6PD), which was designed to examine whether 2-oxoclopidogrel and other components present in the HLMs contributed to anti-platelet activities. The other control (—SH) did not contain any thiol reductant, which was intended to examine whether any metabolites other than the AM and the conjugate interfered with the anti-platelet activity assay. After an incubation of 50 min, the reaction mixtures were centrifuged at 13,000×g to remove the HLMs. The supernatants were loaded onto SPE C18 cartridges to enrich the mixed disulfide conjugates. After extensive washing with water to remove salts and other water-soluble metabolites, the conjugate samples were eluted with 2 ml of methanol. The methanolic fractions were dried using a Speedvac concentrator and the dried samples were then re-suspended in 1 ml of platelet-poor plasma (PPP). Prior to the anti-platelet activity assays, the re-suspended conjugates were divided into two equal volumes (0.5 ml each), one of which was treated with 1 mM GSH at 37° C. for 30 min to generate the AM. Both samples were then placed on ice until use.

The procedures used to determine ex vivo anti-platelet activity were previously reported (see, e.g., Abell L M and Liu E C (2011) J Pharm Exp Ther 339(2):589-596).

Male New Zealand white rabbits (2.2-2.9 kg) were used as blood donors. Whole blood was drawn from a central ear artery into a plastic syringe containing 3.7% sodium citrate as the anticoagulant (1:10 volume ratio of citrate to blood). A whole blood cell count was determined with a Medonic CA620 hematology analyzer (Clinical Diagnostic Solutions, Inc., Plantation, Fla., USA). Platelet-rich plasma (PRP), the supernatant present after centrifugation of whole blood at 100×g for 10 min, was diluted with PPP to achieve a platelet count of approximately 300,000/µl. Platelet-poor plasma was prepared by centrifuging the remaining blood at 1,500×g for 10 min and discarding the bottom cellular layer. The diluted PRP was divided into 0.5 ml samples, centrifuged again at 170×g for 10 mins, and the resulting supernatant was discarded. The platelet pellets were re-suspended in platelet-poor plasma containing the various chemical inhibitors prepared as described previously and incubated with gentle shaking at 37° C. for 60 min to modify the $P2Y_{12}$ receptor. Ex vivo platelet aggregation was assessed by established nephelometric methods with the use of a 4-channel aggregometer (BioData PAP-4; BioData Corp., Horsham, Pa. USA) by recording the increase in light transmission through a stirred suspension of PRP maintained at 37° C. Platelet aggregation was induced with ADP (10 M). A subaggregatory concentration of epinephrine (550 nM) was used to prime the platelets before addition of the agonist.

Example V

This example describes the effects of thiol reductants on the formation of the active metabolite (AM) of clopidogrel. To examine the effects of thiol reductants, the steady-state rates for the formation of the AM in the presence of various thiol reductants was determined. The concentrations of the thiol reductants present in the metabolic reactions were 1 mM except for CPT, DPT and NPT. Instead, the concentrations of these three thiol reductants were 0.3 mM because of their low $K_m$ values. As shown in FIG. 1, the AM is formed in the presence of all but three thiol reductants. The highest rate for the formation of the AM was observed in the presence of GSH, an endogenous reductant in the human body. Specifically, in the presence of 1 mM GSH, the AM is produced at a rate of 167 pmole AM/min/mg HLM. Likewise, L-cysteine is ~84% as active as GSH in producing the AM. As observed previously (see, e.g., Zhang H, et al., (2012) Mol Pharmacol 82:302-309), only a low level of the AM was formed in the presence of 1 mM NAC. The rate is only ~7% of that observed in the presence of 1 mM GSH. No AM was observed in the presence of CPT, DFT, and NPT. Overall the rates for the formation of the AM decrease in the order of GSH>CYS>CG>GC>CYA>BME>NAC>CPT or DFT or NPT. This wide range of rates underscores the critical role of thiol reductants in the formation of the AM.

Example VI

Figure 2:
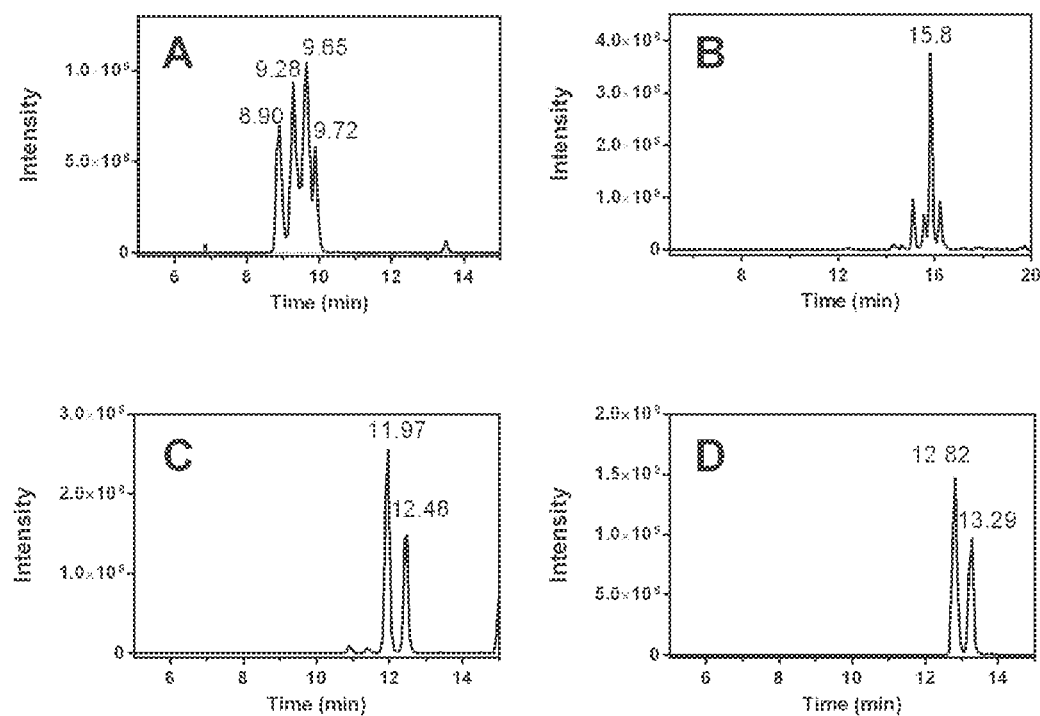
FIG. 2 shows extracted ion chromatograms (EIC) of representative mixed disulfide conjugates of clopidogrel. The mixed disulfide conjugates were produced in 0.2 ml of 50 mM KPi buffer (pH 7.4) containing 1 mg/ml HLMs, 0.1 mM 2-oxoclopidogrel, various thiol reductants and the NADPH-regenerating system at 37° C. for 30 min. MS analyses were performed as described in Materials and Methods. (A), EIC for the BME conjugate at m/z 432.06; (B) EIC for the DFT conjugate at m/z 482.08; (C) EIC for the CPT conjugate at m/z 499.99; (D) EIC for the NPT conjugate at m/z 510.08.

This example describes analyses of the mixed disulfide conjugates of clopidogrel. Formation of the AM was greatly affected by the thiol reductants present. In this experiment, the effects of the thiol reductants on the formation of the mixed disulfide conjugates was examined. This is particularly important in order to understand the cause for the lack of any AM formed in the presence of CPT, DFT, and NPT. In marked contrast to what was observed for the AM, mixed disulfide conjugates were formed in the presence of all the thiol reductants examined. The m/z for the parent ions $MH^+$ and the retention times of these mixed disulfide conjugates are summarized in Table 1, and the extracted ion chromatograms (EICs) of four selected mixed disulfide conjugates are presented in FIG. 2. The parent ions $MH^+$ observed are in excellent agreement with the theoretical values for these conjugates. In the presence of β-mercaptoethanol (BME), four conjugate peaks were observed at m/z 432 eluting from 8.9 to 9.72 min (FIG. 2A). These four AM peaks are likely due to the formation of multiple stereoisomers of clopidogrel as reported previously (see, e.g., Pereillo J M, et al. (2002) Drug Metab Dispos 30(11):1288-1295). Two major conjugate peaks were observed in the presence of CPT and NPT (FIGS. 2C and 4D, respectively). However, in the presence of DFT, one predominant conjugate peak with m/z 482 was observed at 15.8 min (FIG. 2B). The $K_m$ values for the formation of the CPT, NPT and DFT conjugates were determined to be 23, 51 and 30 μM, respectively, which is significantly lower than a $K_m$ of 300 μM for GSH that we previously reported (see, e.g., Zhang H, et al., (2012) Mol Pharmacol 82:302-309).

TABLE 1

Parent ions ($MH^+$) and retention times (RT) observed for the mixed disulfide conjugates of clopidogrel in LC-MS analysis.

| Thiol Compounds | Abbreviation | $MH^+$ (m/z) | $RT^a$ (min) | $MH^+$ Theoretical[b] (m/z) |
|---|---|---|---|---|
| Glutathione | GSH | 661.05 | 5.47 | 661.02 |
| L-cysteine | CYS | 475.05[c] | 5.60[c] | 475.06 |
| L-cysteine-L-glyceine | CG | 532.09 | 5.44 | 532.10 |
| γ-L-glatamyl-L-cysteine | GC | 604.09 | 5.71 | 604.12 |
| cysteamine | CYA | 431.05 | 6.33 | 431.09 |
| β-mercaptoethanol | BME | 432.06 | 9.65 | 432.07 |
| N-acetyl-L-cysteine | NAC | 517.11 | 6.85 | 517.09 |
| 6-chloropyridazine-3-thiol | CPT | 499.99 | 11.97 | 500.03 |

TABLE 1-continued

Parent ions (MH+) and retention times (RT) observed for the mixed disulfide conjugates of clopidogrel in LC-MS analysis.

| Thiol Compounds | Abbreviation | MH+ (m/z) | RT[a] (min) | MH+ Theoretical[b] (m/z) |
|---|---|---|---|---|
| 2,5-dimethylfuran-3-thiol | DFT | 482.08 | 15.80 | 482.09 |
| 3-nitropyridine-2-thiol | NPT | 510.08 | 12.82 | 510.06 |

[a]retention time for the most intense peak;
[b]exact masses calculated from molecular formula;
[c]data from Zhang H, et al., (2012) Mol Pharmacol 82: 302-309.

Figure 3:
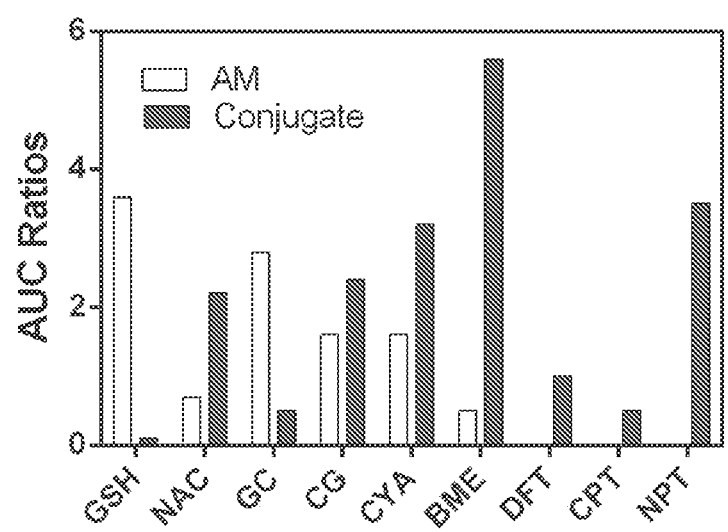
FIG. 3 shows relative amounts of the AM and thiol conjugates of clopidogrel produced by HLMs. The AM and conjugates were produced in 0.2 ml of 50 mM KP (pH 7.4) as described in FIG. 2. For these analyses, 50 pmoles of (S)-clopidogrel was spiked into each sample as the IS. Both the AM and the thiol conjugates were analyzed using LC-MS/MS in the dependent scan mode as described in Materials and Methods. Legend: open bar, AUC ratio of m/z 356 (AM) to m/z 322 (IS); solid bar, AUC ratios of respective conjugate to IS.

Integration of the area under the curve (AUC) for each EIC of the conjugates gave the relative amount of the mixed disulfide conjugates produced. As shown in FIG. 3, the relative amounts of the mixed disulfide conjugates varied substantially from each other. Only a low level of the glutathionyl conjugate was formed, indicating that metabolism of 2-oxoclopidogrel in the presence of GSH greatly favors the formation of the AM. Although both the AM and the mixed disulfide conjugate were formed in the presence of BME, it is clear that formation of the conjugate is favored over the AM. In spite of lack of formation of the AM, the mixed disulfide conjugates of CPT, DFT and NPT were formed in significant quantities. Due to lack of genuine standards of these conjugates it was unable to quantitate the absolute amounts of these conjugates. Caution should be exercised in comparing the absolute amounts of the conjugates based on the AUC ratios because these conjugates may respond differently to the MS detector.

Figure 4:
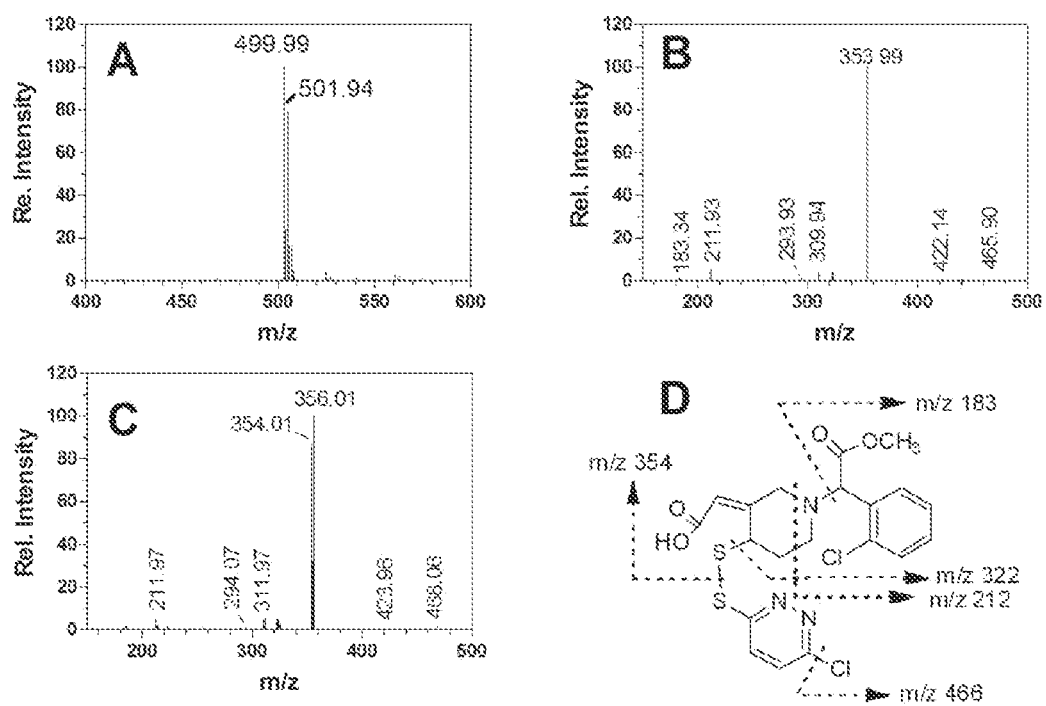
FIG. 4 shows MS and $MS^2$ spectra of the mixed disulfide conjugate of CPT. The conjugate was produced as described in FIG. 2. The MS and $MS^2$ spectra were obtained using LC-MS/MS in the dependent-scan mode as described in Materials and Methods. (A), MS spectrum of the CPT conjugate; (B) $MS^2$ spectrum of the parent ion m/z 499.99 for the CPT conjugate; (C), MS' spectrum of the parent ion m/z 501.94 for the CPT conjugate; (D), assignments for the fragmentation pattern shown in FIG. 4B.

To determine the chemical structure of these conjugates, the MS and $MS^2$ spectra were obtained. The MS spectra of all ten conjugates showed the major MH+ peaks at expected m/z ratios as summarized in Table 1, along with a pair of $^{35}Cl/^{37}Cl$ isotope peaks that is characteristic of the presence of one Cl atom in clopidogrel. The only exception to this is the CPT conjugate that contains two chlorine atoms. Its MS and $MS^2$ spectra are shown in FIG. 4. This conjugate was observed at m/z 499.99, which is within an experimental error of 80 ppm of the expected m/z value of 500.03. In addition, a strong isotope peak was also observed at 501.94 with ~75% of the intensity of the base peak, indicative of the presence of two chlorine atoms in this conjugate. The $MS^2$ of the parent ion at m/z 499.99 showed the formation of multiple daughter ions. The predominant daughter ion was observed at m/z 353.99 with other minor ones at m/z 465.90, 211.93 and 183.34. This fragmentation pattern, in addition to the presence of the $^{35}Cl/^{37}Cl$ isotope peaks, is consistent with the chemical structure of the conjugate possessing a mixed disulfide bond shown in FIG. 4D. The predominant daughter ion m/z 353.99 is assigned to the larger fragment cleaved at the mixed disulfide bond as we reported previously for the conjugates of GSH, NAC and L-cysteine with clopidogrel (see, e.g., Zhang H, et al., (2012) Mol Pharmacol 82:302-309). The daughter ions at m/z 212 and 183 are also characteristic of clopidogrel (see, e.g., Dansette P M, et al., (2010) Chem Res Toxicol 23(7):1268-1274; Pereillo J M, et al., (2002) Drug Metab Dispos 30(11):1288-1295). The $MS^2$ spectrum of the isotope peak at m/z 501.94 provides further evidence for this assignment. As shown in FIG. 4C, a pair of daughter ions, instead of single ions, were observed two mass units apart, which support the presence of two chlorine atoms. The $MS^2$ spectra for the rest of the conjugates exhibited very similar fragmentation patterns with the characteristic daughter ions at m/z 354.

Example VII

This example describes the kinetics for the reduction of the mixed disulfide conjugates of clopidogrel by GSH. The kinetics for the thiol-disulfide exchange reaction between the various mixed disulfide conjugates and GSH were determined and the results are shown in FIG. 5. Incubation of the conjugates with GSH and cytosol led to time-dependent decreases in the amounts of the mixed disulfide conjugates (FIG. 5A). Fitting the kinetic data to a mono-exponential function gave first order rate constants of 0.07, 0.79, 0.43, 1.65 and 0.13 $min^{-1}$ for the losses of the mixed disulfide conjugates of BME, CPT, NAC, DFT and NPT, respectively. Since these kinetics were determined under pseudo first order conditions with excess of GSH (1 mM), these rate constants are equivalent to the second order rate constants of 1.2, 13, 7.2, 28 and 2.2 $M^{-1}s^{-1}$, respectively. The data also demonstrated the variable reactivity of these conjugates toward GSH. The DFT and CPT conjugates are 10 to 20-fold more reactive than the BME conjugate, respectively. It appears, for example, that ~50% of the BME conjugate still remained even after an incubation of 40 min, indicating, for example, that the thiol-disulfide exchange for this conjugate had reached equilibrium.

To examine the effect of cytosol and to monitor the conjugates and the AM simultaneously, the kinetics for both the formation of the AM and the reduction of the CPT conjugate in the presence and absence of cytosol was determined. As shown in FIG. 5B, the decrease in the amount of the CPT conjugate occurred with concomitant increase in the amount of the AM with almost identical rate constants. In the presence of cytosol, the rate constants for the reduction of the conjugate and for the formation of the AM are 0.73 and 0.50 $min^{-1}$ respectively. In the absence of cytosol, the reduction of the CPT conjugate is approximately one-half as fast with a rate constant of 0.39 $min^{-1}$ for the reduction of the conjugate and 0.35 $min^{-1}$ for the formation of the AM. This indicates that the cytosol accelerates the reduction of the thiol-disulfide exchange reaction as observed previously (see, e.g., Hagihara K, et al., (2012) Drug Metab Dispos 40(9): 1854-1859; Hagihara K, et al., (2011) Drug Metab Dispos 39(2):208-214).

Example VIII

Figure 6:
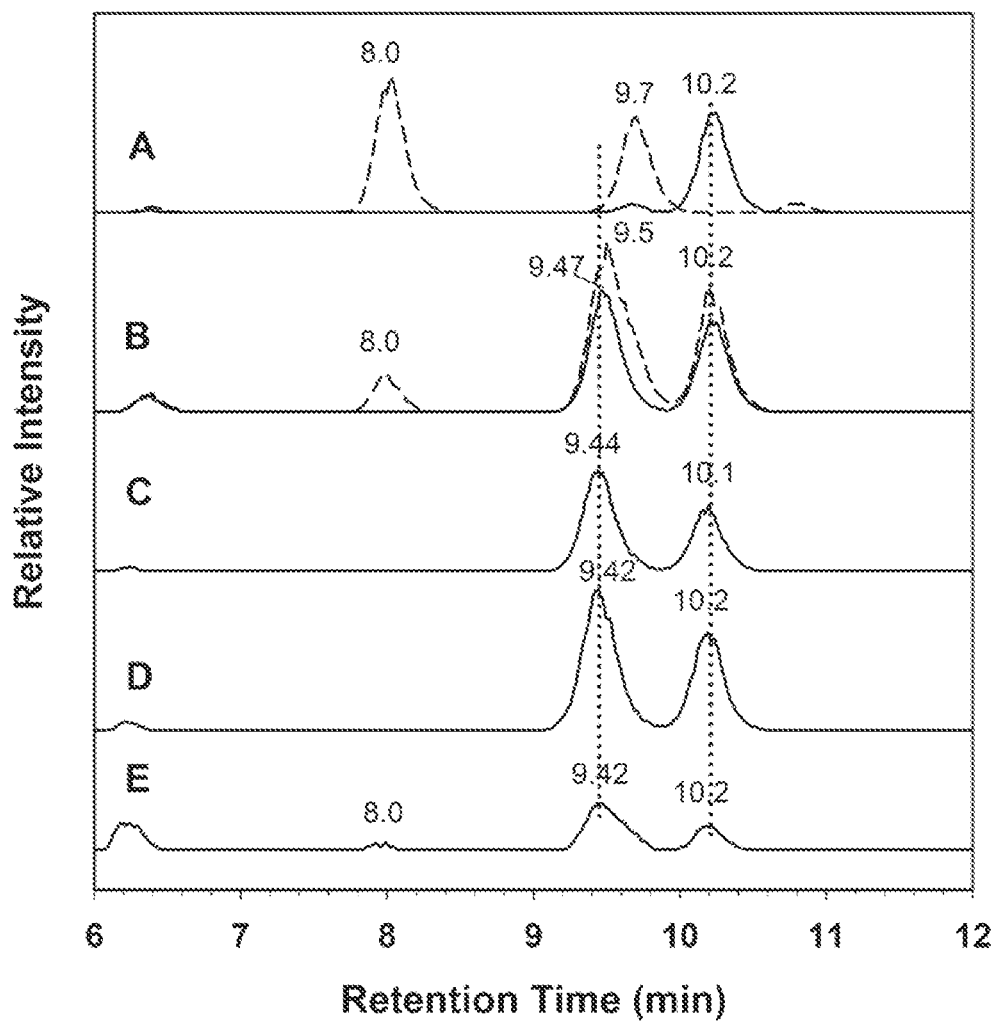
FIG. 6 shows extracted ion chromatograms observed at m/z 504 showing the formation of the active metabolite H4 from the mixed disulfide conjugates of clopidogrel. The mixed disulfide conjugates were produced in the HLMs and purified with SPE cartridges as described in FIG. 3. Prior to MS analyses, the mixed disulfide conjugates were treated with DTT to release the AM that was then subsequently derivatized with MPB. The AM-MP derivatives were analyzed using LC-MS/MS as described in Materials and Methods. Legend: A, trans- (dashed line) and cis-clopidogrel-MP (solid line) standards; B, the AM-MP obtained in the presence of 1 mM GSH (dashed line) and 1 mM ascorbic acid (solid line); C, the AM-MP obtained from the CPT conjugate; D, the AM-MP obtained from the NPT conjugate; E, the AM-MP obtained from the DFT conjugate. The amplitude was multiplied by two.

This example describes formation of active metabolite H4 from the mixed disulfide conjugates of clopidogrel. As shown in Scheme 2, the active metabolite contains two chiral centers (C7 and C4) and one double bond (C3-C16). Therefore, metabolism of racemic 2-oxoclopidogrel could potentially produce up to eight stereoisomers. However, only four of the diastereomers, historically referred to as H1, H2, H3 and H4, can be separated on conventional reverse phase C18 columns, whereas the other four stereoisomers co-elute as enantiomers. It has been established that H4 is responsible for the anti-platelet activity in humans and that the double bond of H4 is in cis configuration (see, e.g., Pereillo J M, et al., (2002) Drug Metab Dispos 30(11):1288-1295; Savi P, et al., (2000) Thromb Haemost 84(5):891-896: Tuffal G, et al., (2011) Thromb Haemost 105(4):696-705). To evaluate the therapeutic potential of these conjugates, whether H4 is formed in the mixed disulfide conjugates was examined and the results presented in FIG. 6.

The metabolism of 2-oxoclopidogrel by HLMs in the presence of GSH led to the formation of four stereoisomers eluting between 8 to 11 min (dashed line, FIG. 6B). Based on the order of elution of the AM-MP derivatives on reverse phase C18 columns (see, e.g., Tuffal G, et al., (2011) Thromb Haemost 105(4):696-705), it is likely that the isomer eluting at 10.2 min is the cis isomer of H4. This is consistent with the retention time of the cis-clopidogrel-MP standard shown in FIG. 6A (solid line). Likewise the MP derivatives of the DFT conjugate also exhibited four peaks, similar to those observed in the presence of GSH, indicating that the DFT conjugate produced the cis isomers of the AM following the thiol-exchange reaction. In contrast, the MP derivative of the CPT and NPT conjugates showed two major peaks at 9.4 and 10.2 min, which is consistent with the selective formation of the active isomer H4 (FIGS. 6C & D).

Example IX

Figure 7:
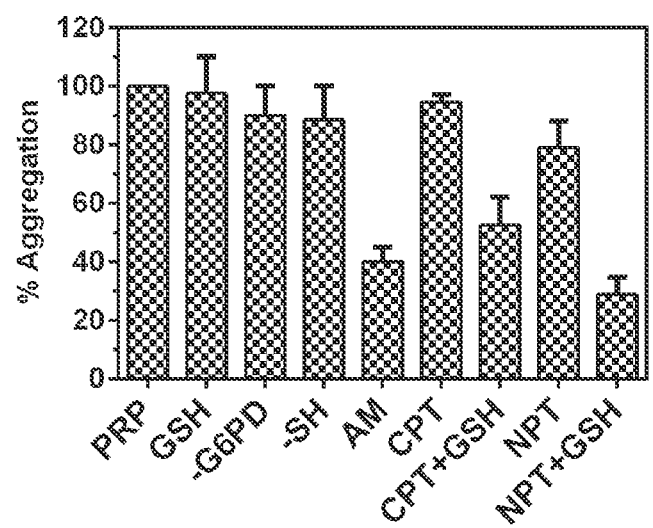
FIG. 7 shows inhibition of platelet aggregation by the mixed disulfide conjugates of clopidogrel. The mixed disulfide conjugates were prepared and purified from the reaction mixtures in the presence of 0.3 mM CPT and NPT, along with three control samples containing either 1 mM GSH, no thiol reductant or no G6PD. All samples were re-suspended in 0.5 ml PPP, some of which were treated to 1 mM GSH to release the AM. Platelet aggregation was initiated by the addition of 10 μM ADP and recorded with an aggregometer. The percentage of aggregation was normalized to that of PRP and averaged over four separate measurements. For details, see Materials and Methods. Legend: PRP, untreated platelet-rich plasma; GSH, 1 mM GSH in PRP; -G6PD, metabolites produced in the absence of G6PD; —SH, metabolites produced in the absence of any thiol reductants; GSH, metabolites produced in the presence of 1 mM GSH; CPT, metabolites produced in the presence of 0.3 mM CPT; CPT+GSH, metabolites produced in the presence of 0.3 mM CPT and then treated with 1 mM GSH; NPT, metabolites produced in the presence of 0.3 mM NPT; NPT+GSH, metabolites produced in the presence of 0.3 mM NPT and then treated with 1 mM GSH.

This example describes anti-platelet activity of the mixed disulfide conjugates of CPT and NPT. As a proof of concept, the anti-platelet activities of two of the mixed disulfide conjugates, the CPT and NPT conjugates, were examined for several reasons. First, both conjugates can be generated without the formation of any AM, which eliminates any interference from the AM during the anti-platelet activity assays. Second, both conjugates exchange thiols with GSH at relatively fast rates, which avoids potential decay of the AM. Third, reduction of the two conjugates produces the H4 isomer that is known responsible for the anti-platelet activity in humans. The results for the ex vivo anti-platelet activity assays are shown in FIG. 7. The percentage of aggregation was normalized to that of PRP to compensate for any variations due to environmental factors such as blood sources, PRP preparations, etc. As shown, the three control samples showed no inhibition of the platelet aggregation. The first control showed that free GSH has no effect on platelet aggregation at 1 mM concentration (GSH, FIG. 7), and the second control showed that non-metabolite components present in the reaction mixtures such as 2-oxoclopidogrel and related impurities did not inhibit platelet aggregation (-G6PD, FIG. 7). It is known that clopidogrel may decompose to byproducts via non-enzymatic oxidation (see, e.g., Mohan A, et al., (2008) J Pharm Biomed Anal 47(1): 183-189; Fayed A S, et al., (2009) J Pharm Biomed Anal 49(2):193-200). These byproducts do not seem to have any inhibitory effects on platelet aggregation. In the third control it was demonstrated that the metabolites from the reaction mixture in the absence of any thiol reductants have no effects on platelet aggregation either. However, ~60% inhibition of platelet aggregation in the sample prepared from the reaction mixture containing GSH was observed (AM, FIG. 7). This is expected since metabolism of 2-oxoclopidogrel in the presence of 1 mM GSH generates the AM as shown in FIG. 1. Incubation of PRP with the CPT and NPT conjugates did not inhibit platelet aggregation, indicating that the conjugates themselves have no anti-platelet activity (CPT & NPT, FIG. 7). In marked contrast, incubation of PRP with the CPT and NPT conjugates that had been treated with 1 mM GSH significantly inhibited platelet aggregation by ~50 and 70%, respectively. This inhibitory activity most likely arises from the AM released from the conjugates by GSH. These results demonstrate that the conjugates of clopidogrel have no anti-platelet activity and also confirmed that the AM is solely responsible for the inhibition of platelet aggregation. Furthermore, they demonstrate that it is possible to deliver the AM without the need for bioactivation by polymorphic P450s. It is noteworthy to point out that the variations in the percentage of aggregation observed in the GSH, CPT+GSH, and NPT+GSH samples are most likely due to variations in the concentrations of the AM. It was estimated that the concentrations of the AM in these samples were in the range of 1-4 µM.

Example X

This example describes in vivo antiplatelet activity of mixed disulfide conjugates of clopidrogrel. The antiplatelet activity of the mixed disulfide conjugates of clopidogrel was determined in male New Zealand (NZ) white rabbits through intravenous injection. The mixed disulfide conjugates were bio-synthesized using the following technique.

Part I. Bio-Synthesis of Mixed Disulfide Conjugates of Clopidogrel

Mixed disulfide conjugates of clopidogrel were synthesized in a reconstituted system containing recombinant cytochrome P450 2C19 (CYP2C19) and other essential components. CYP2C19 converted 2-oxoclopidogrel to a mixed disulfide conjugate in the presence of respective thiol compound in reconstituted systems. Scheme 5 illustrates the bio-synthesis of the mixed disulfide conjugate between clopidogrel and 3-nitropyridine-2-thiol, referred to as clopNPT.

Scheme 5.
Biosynthesis of the mixed disulfide conjugate of clopidogrel clopNPT.

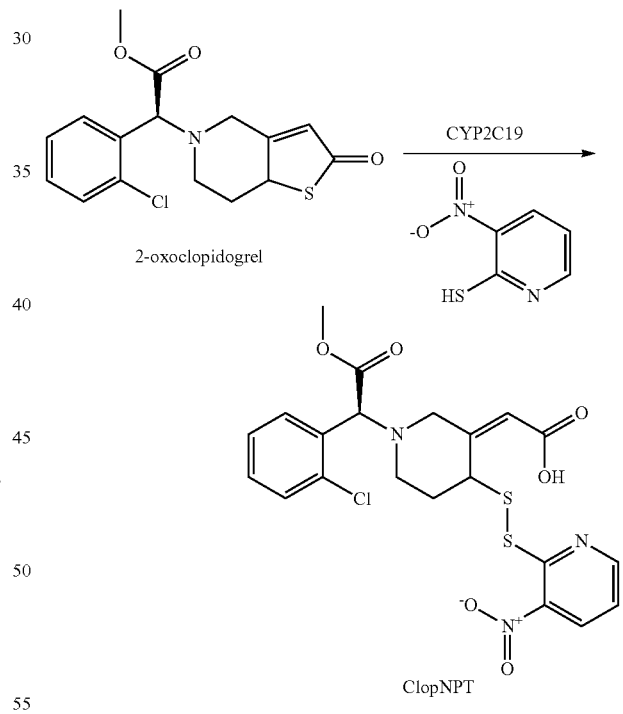

In a typical reaction, 50 nmoles of CYP2C19, 150 nmoles of P450 reductase and 250 nmoles of cytochrome b5 were reconstituted in phospholipid vesicles to form active protein complexes. 2-oxoclopidogrel and 3-nitropyrine-2-thiol were added at final concentrations of 0.05 and 0.3 mM respectively. Bio-synthesis of clopNPT was initiated by the addition of 1 mM NADPH. The reaction was incubated at 37° C. for 2 hours.

Figure 8:
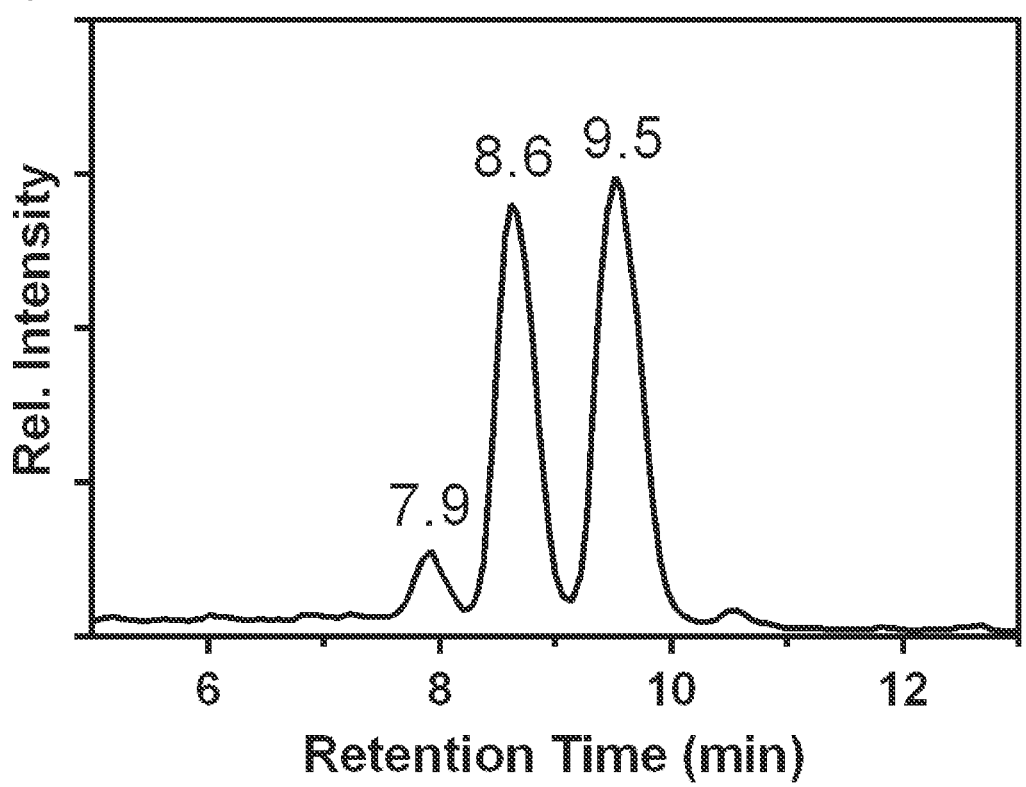
FIG. 8 presents a total ion chromatogram of pure (S)-clopNPT bio-synthesized in the reconstituted systems as described in Example X. The three diastereomers of (S)-clopNPT were eluted at 7.9, 8.6, and 9.5 min.

To purify clopNPT, the reaction mixture containing clopNPT was first filtered through a membrane with a cutoff of 10 kDa to remove all protein components. The filtrate containing clopNPT was then enriched on solid phase extraction (SPE) cartridges. ClopNPT was eluted from the SPE cartridges with 80% methanol/20% water. The eluent was concentrated to 5 ml at 50° C. under vacuum. The concentrated mixture was loaded on a preparative reverse phase C18 column and ClopNPT was purified using high pressure liquid chromatography (HPLC). ClopNPT was eluted from the preparative C18 column at a flow rate of 3 ml/min with isocratic mobile phase consisting of 42% methanol/35% acetonitrile/22.9% water/0.1% formic acid. The HPLC fractions containing clopNPT were pooled and dried under vacuum. The final yield was ~25%. The purity of clopNPT estimated with liquid chromatography-tandem mass spectrometry (LC-MS/MS) was >90% as shown in FIG. 8.

Part II. Anti-Platelet Activity of Mixed Disulfide Conjugates of Clopidogrel

The antiplatelet activity of the mixed disulfide conjugates of clopidogrel was determined using male NZ white rabbits (1.2-1.25 kg).

To prepare intravenous solution, (S)-clopNPT was dissolved at 0.7 mg/ml in a mixture of N,N-dimethylacetamide (DMA), polyethylene glycol (PEG) 400, and saline at 5, 15 and 80 (v/v) ratio. The male NZ white rabbits were dosed at 2 mg/kg of (S)-clopNPT using two different methods. In Method 1, the intravenous solution was first mixed with 5 mM glutathione. After an incubation of 15 min at 37° C. to activate (S)-clopNPT, the mixture was intravenously injected to the rabbit via the jugular vein. In Method 2, the male NZ white rabbit was fed with 5 ml of Readisorb glutathione solution once daily for three days to increase cellular glutathione concentrations. On the third day, (S)-clopNPT dissolved in DMA/PEG400/saline was injected intravenously to the Readisorb-treated rabbit. As a negative control, (S)-clopidogrel was dosed intravenously to a male NZ white rabbit at 2 mg/kg as well. Prior to and 1 and 2 hours after dosing (S)-clopNPT, whole blood was drawn from the carotid artery into a plastic syringe containing 3.7% sodium citrate as the anticoagulant (1:10 volume ratio of citrate to blood). A whole blood cell count was determined with a Medonic CA620 hematology analyzer (Clinical Diagnostic Solutions, Inc., Plantation, Fla., USA). Platelet-rich plasma (PRP), the supernatant present after centrifugation of whole blood at 100×g for 10 min, was diluted with platelet-poor plasma (PPP) to achieve a platelet count of approximately 300,000/1. Platelet-poor plasma was prepared by centrifuging the remaining blood at 1,500×g for 10 min and discarding the bottom cellular layer. The diluted PRP was divided into 0.5 ml samples, centrifuged again at 170×g for 10 mins, and the resulting supernatant was discarded. Platelet aggregation was assessed by established nephelometric methods with the use of a 4-channel aggregometer (BioData PAP-4; BioData Corp., Horsham, Pa., USA) by recording the increase in light transmission through a stirred suspension of PRP maintained at 37° C. Platelet aggregation was induced with ADP (10 μM). A subaggregatory concentration of epinephrine (550 nM) was used to prime the platelets before addition of the agonist.

Figure 9:
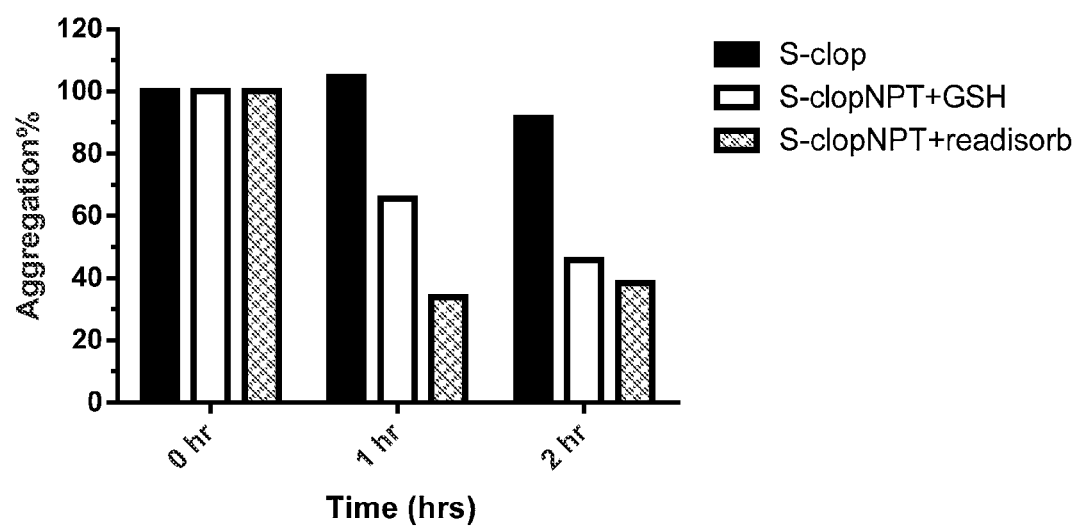
FIG. 9 presents platelet activities of male NZ white rabbits following IV injection of (S)-clopNPT as described in Example X.

The results are presented in FIG. 9. As shown, (S)-clopidogrel did not inhibit platelet aggregation at a dose of 2 mg/kg. However, (S)-clopNPT strongly inhibited platelet aggregation since more than 50% of the platelet aggregation was inhibited by (S)-clopNPT regardless whether (S)-clopNPT was dosed with glutathione or Readisorb glutathione. These results demonstrated that (S)-clopNPT conjugate can be activated either by extraneous glutathione or endogenous glutathione. It is evident that endogenous glutathione is more effective in activating (S)-clopNPT because the platelet activity of the Readisorb-treated rabbit is inhibited by ~70% within one hour of IV injection. Numerous studies have shown the beneficial effects of glutathione in heart disease and stroke, anti-oxidative stress, aging, etc. Co-administration of glutathione and the mixed disulfide conjugates of clopidogrel likely offers not only the benefit of (S)-clopNPT as antiplatelet agents, but also the benefits associated with the use of glutathione alone.

These results demonstrate that the mixed disulfide conjugates of clopidogrel are more effective antiplatelet agents than clopidogrel.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

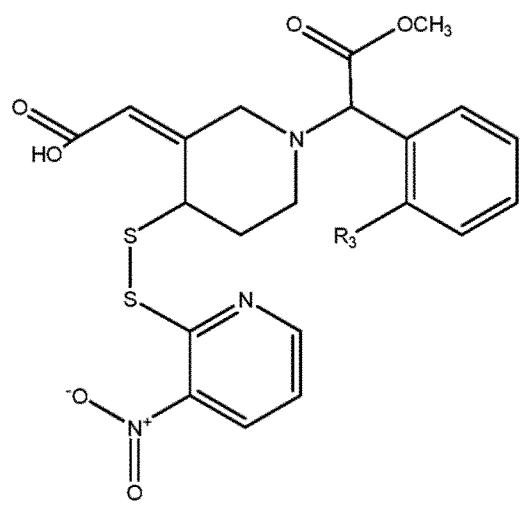

What is claimed is:

1. A compound having Formula I:

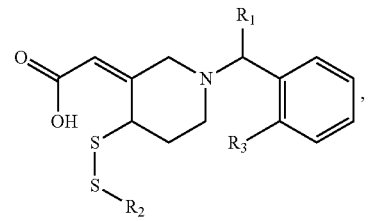

or a pharmaceutically acceptable salt or solvate thereof;
wherein R1 is selected from the group consisting of H, —CO—OCH3, and

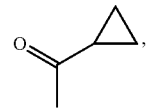

wherein R2 is selected from the group consisting of

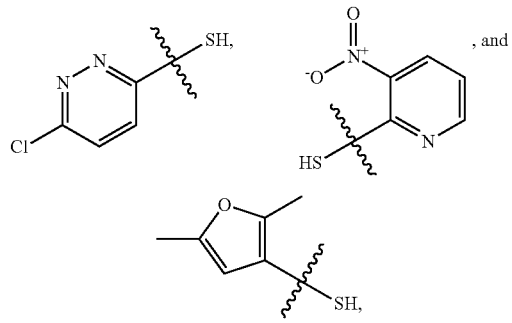

wherein R3 is Chlorine or Fluorine.

2. A pharmaceutical composition comprising a compound of claim 1 and a pharmaceutically acceptable carrier.

3. The pharmaceutical composition of claim 2, wherein said pharmaceutical composition is configured for intravenous administration.

4. The compound of claim 1, wherein said compound is selected from the group consisting of

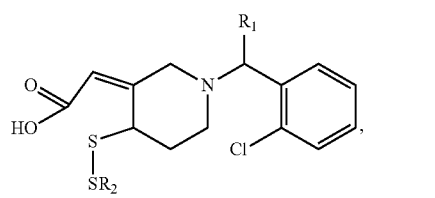

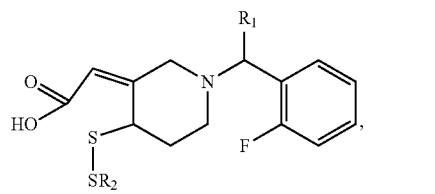

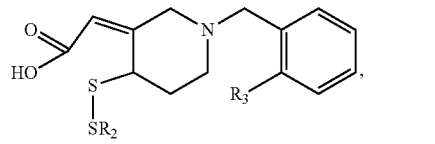

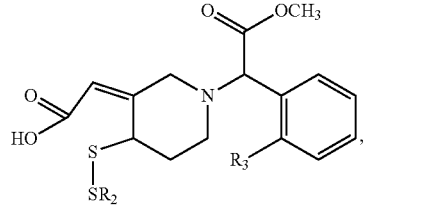

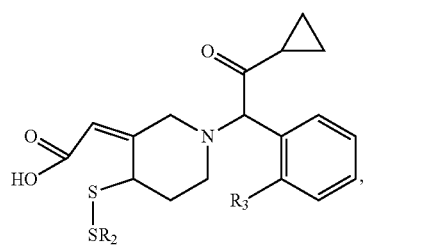

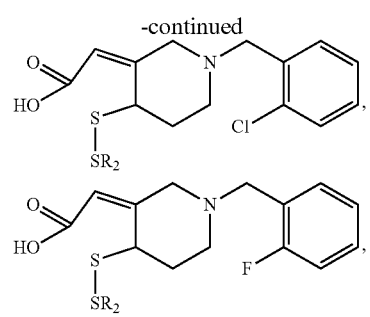

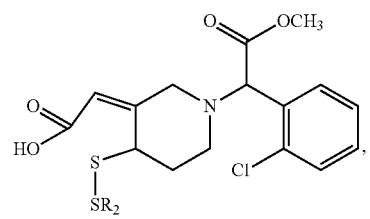

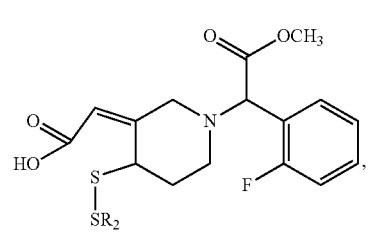

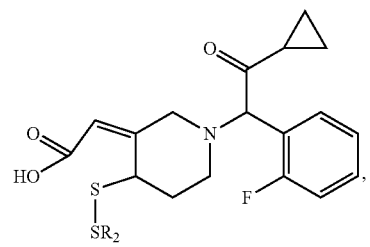

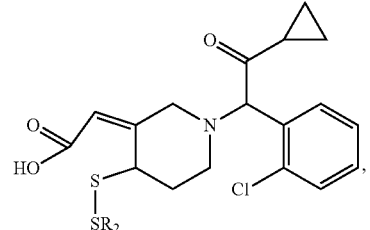

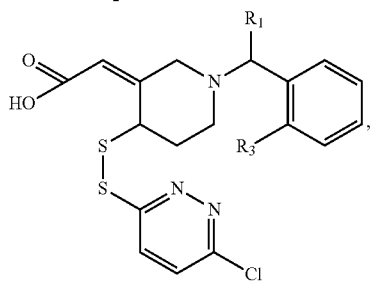

61
-continued
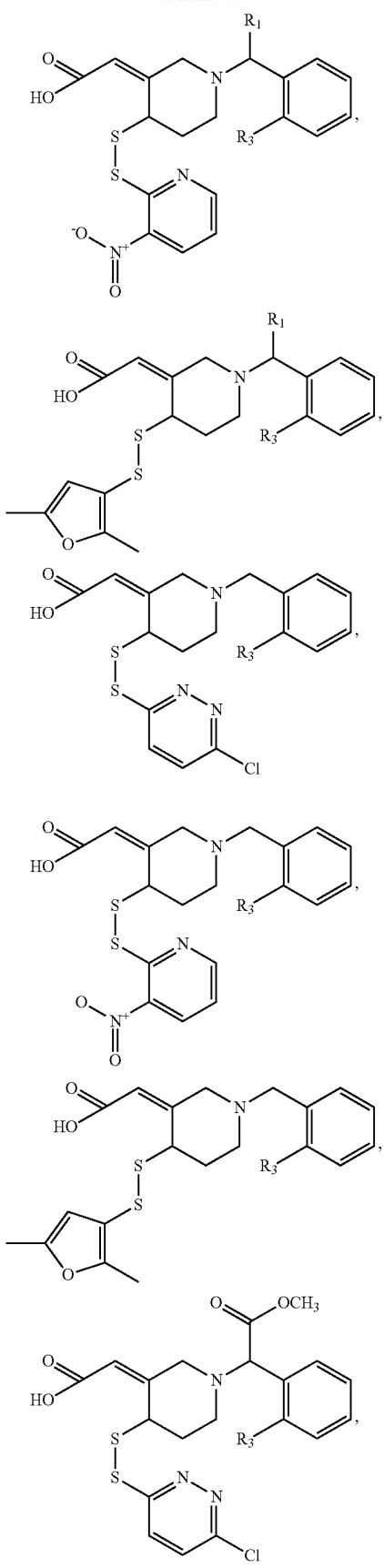
62
-continued
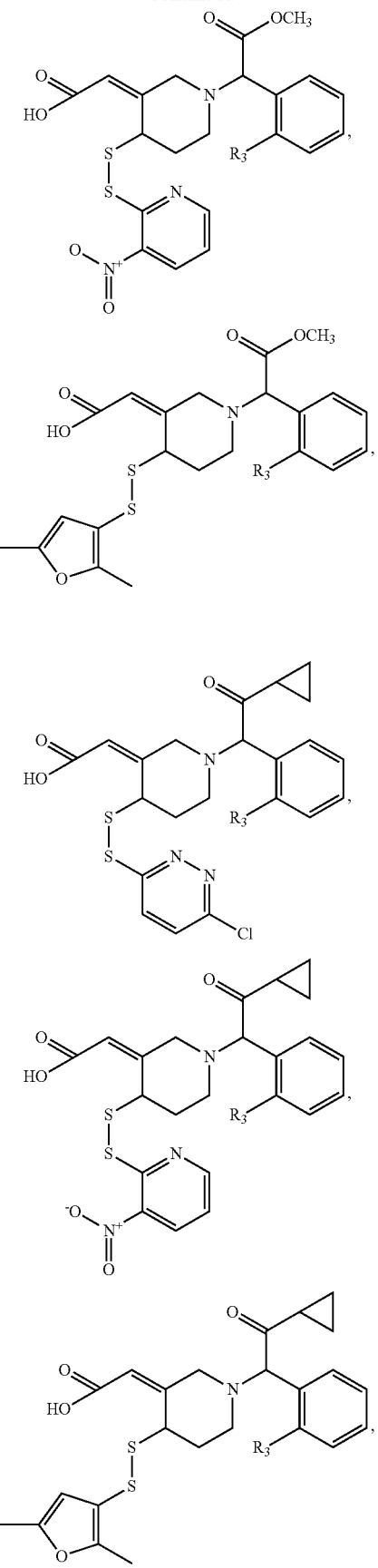

-continued
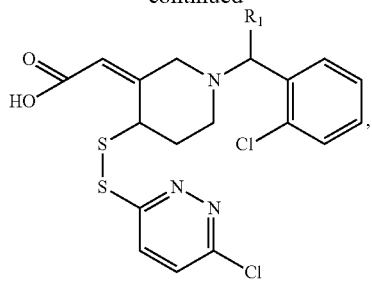
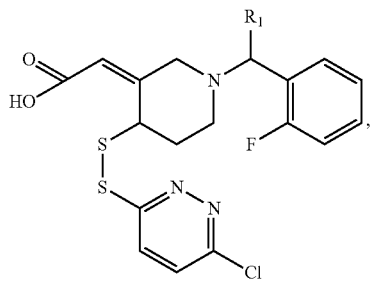
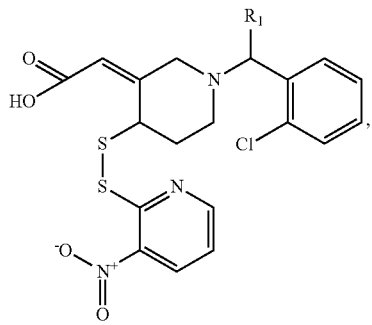
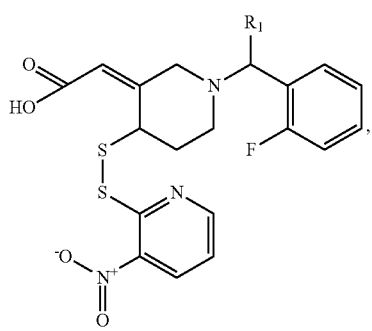
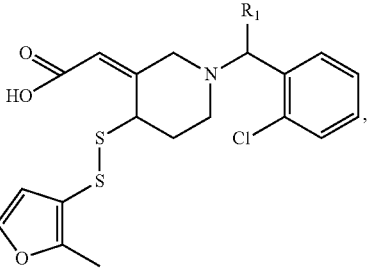
, and
-continued
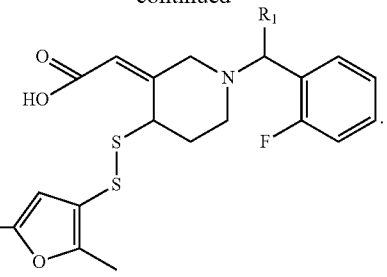
5. The compound of claim 1, wherein said compound is selected from the group consisting of:
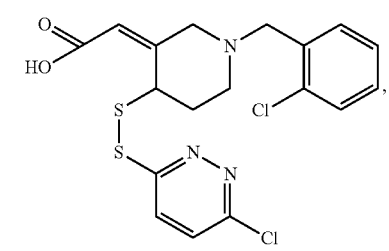
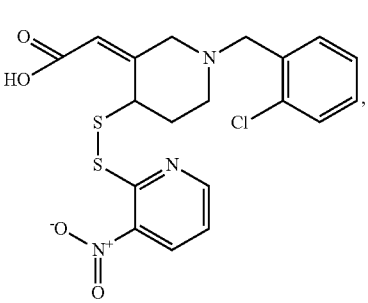
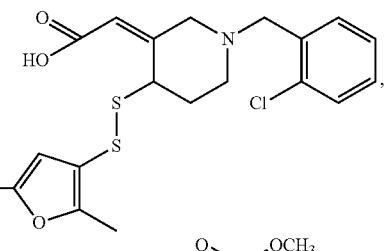
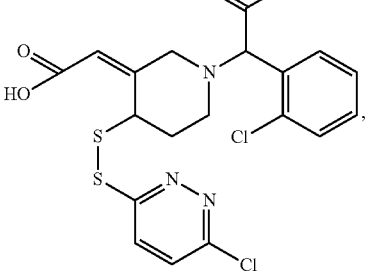

65
-continued
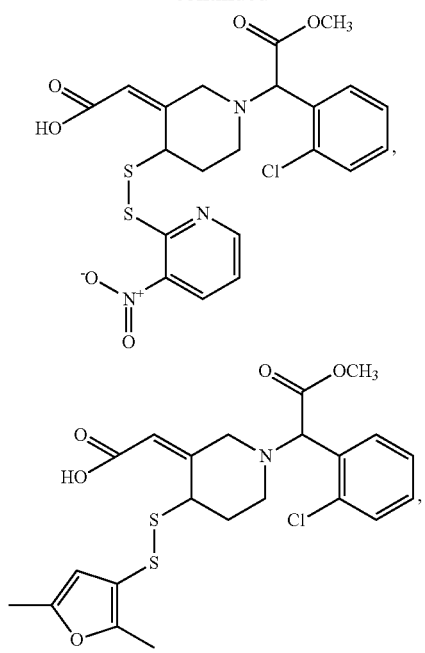
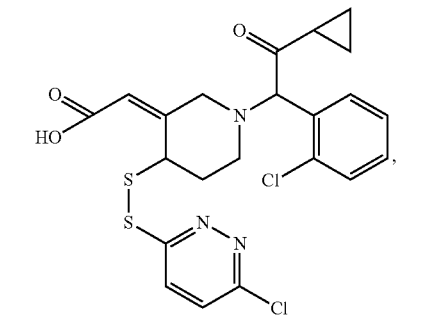
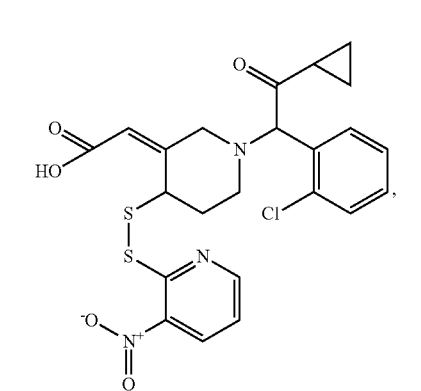
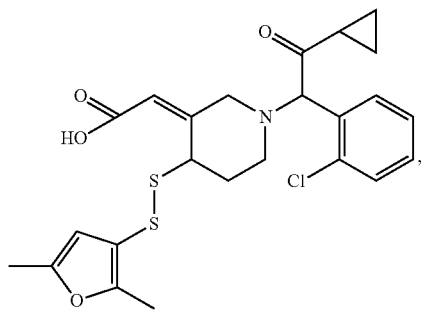
66
-continued
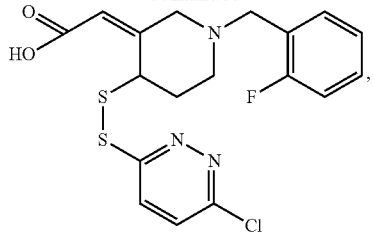
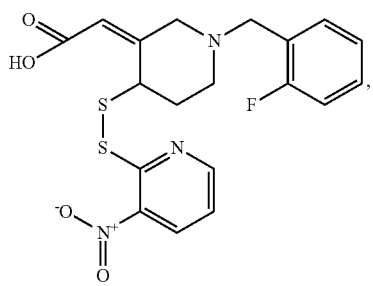
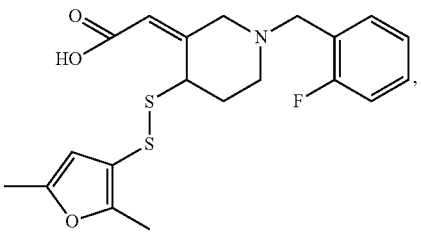
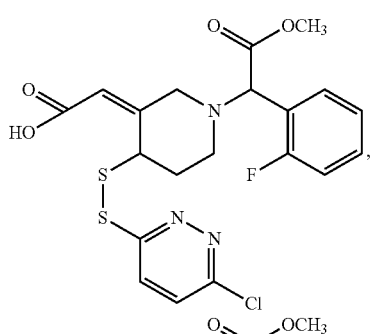
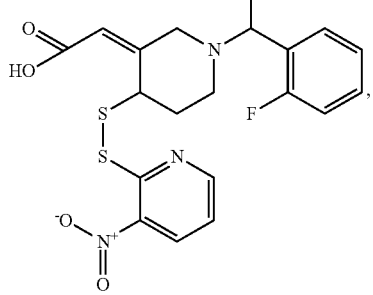

-continued
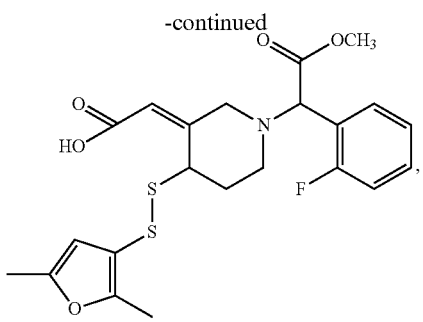
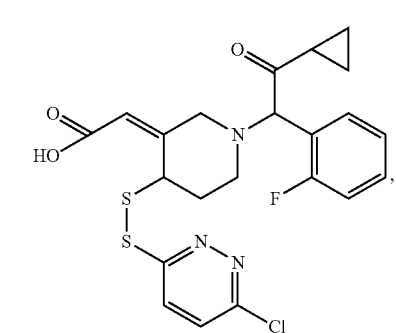
-continued
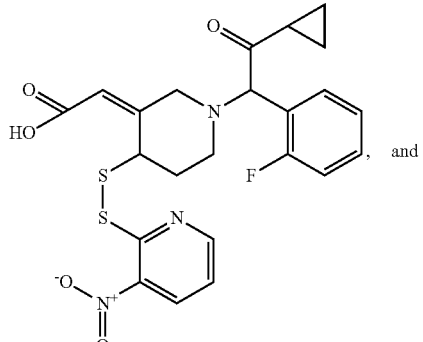
and
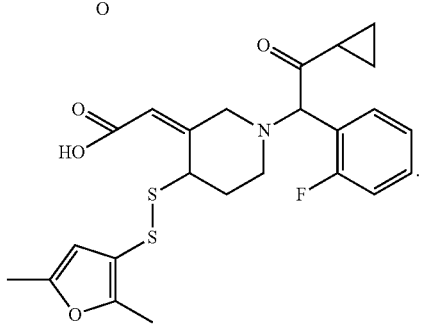
* * * * *

UNITED STATES PATENT AND TRADEMARK OFFICE
CERTIFICATE OF CORRECTION

PATENT NO. : 9,718,778 B2
APPLICATION NO. : 14/758736
DATED : August 1, 2017
INVENTOR(S) : Haoming Zhang and Paul Hollenberg Page 1 of 2

It is certified that error appears in the above-identified patent and that said Letters Patent is hereby corrected as shown below:

In the Claims

Column 61, Claim 4, Lines 35-45 reads:

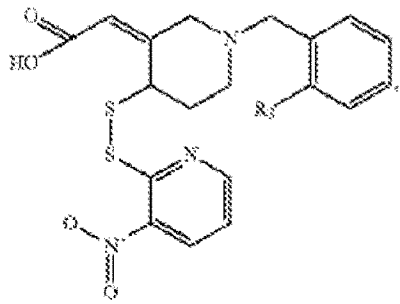

Whereas it should read:

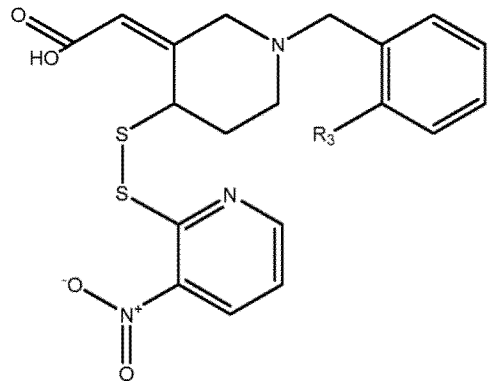

Signed and Sealed this
Seventh Day of August, 2018

Andrei Iancu
*Director of the United States Patent and Trademark Office*

CERTIFICATE OF CORRECTION (continued)
U.S. Pat. No. 9,718,778 B2

Column 62, Claim 4, Lines 1-15 reads:

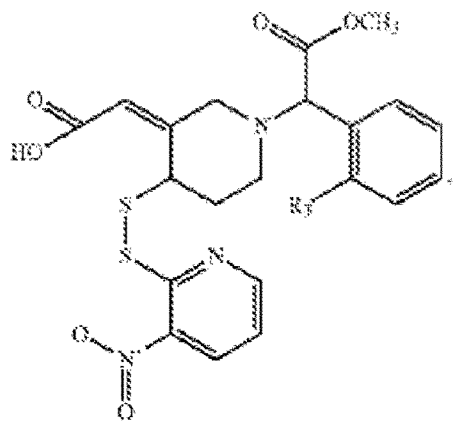

Whereas it should read: